(12) United States Patent
Atsumi et al.

(10) Patent No.: US 6,487,468 B1
(45) Date of Patent: Nov. 26, 2002

(54) METHOD FOR ANALYZING FORGING PROCESS AND MEDIUM STORING PROGRAM FOR EXECUTING THE METHOD

(75) Inventors: Yoshitaka Atsumi, Toyota (JP); Naoki Matsuoka, Chiryu (JP); Tadao Akashi, Toyota (JP); Hiroshi Yano, Nishikamo-gun (JP); Masahiko Takeuchi, Toyota (JP); Kokichi Nakanishi, Aichi (JP)

(73) Assignees: Toyota Jidosha Kabushiki Kaisha, Toyota (JP); Kabushiki Kaisha Toyota Chuo Kenkyusho, Aichi-ken (JP)

( * ) Notice: Subject to any disclaimer, the term of this patent is extended or adjusted under 35 U.S.C. 154(b) by 0 days.

(21) Appl. No.: 09/429,162

(22) Filed: Oct. 28, 1999

(30) Foreign Application Priority Data

Oct. 30, 1998 (JP) ............................................ 10-309920
Aug. 6, 1999 (JP) ............................................ 11-223755

(51) Int. Cl.$^7$ ............................................... G06F 19/00
(52) U.S. Cl. ........................... 700/97; 700/110; 73/804; 703/9
(58) Field of Search ............................ 700/45, 29, 98, 700/197, 175, 110; 703/9, 6; 73/804, 863, 783, 866, 898; 72/422, 308

(56) References Cited

U.S. PATENT DOCUMENTS

| 4,796,456 A | * | 1/1989 | Schmoll et al. ................ 72/402 |
| 4,967,584 A | * | 11/1990 | Sato et al. ...................... 72/352 |
| 5,402,366 A | | 3/1995 | Kihara et al. ................ 700/197 |
| 6,306,231 B1 | * | 10/2001 | Sakamoto et al. .......... 148/666 |

FOREIGN PATENT DOCUMENTS

| JP | 9-220634 | 8/1997 |
| JP | 2775538 | 5/1998 |

OTHER PUBLICATIONS

Managnan, L., "Simulation Tridimensionnelle Des Procedes De Mise En Forme Des Pieces Brutes", Ingeniers De L'Automobile, No. 709 Nov. 1996, pp. 76, 78–80.

Tekkaya, A. E., "Stand Und Entwicklungstendenzen Der Umformsimilation", Umformtechnik, vol. 32, No. 2, Apr. 1998, pp. 44–48.

Patent Abstracts of Japan, vol. 2000, No. 1, Oct. 1999, No. JP 11 272887 A (Nissan Motor Co Ltd.).

Patent Abstracts of Japan, vol. 016, No. 157 (M–1236), Jan. 1992, No. JP 04 009242 A (Toyota Motor Corp.).

* cited by examiner

*Primary Examiner*—Maria N. Von Buhr
*Assistant Examiner*—Kidest Bahta
(74) *Attorney, Agent, or Firm*—Pillsbury Winthrop LLP

(57) ABSTRACT

In a forging process analyzing method, many trace points are set in a workpiece. Lines connecting the trace points express fiber flow lines. The fiber flow lines may be imaginary ones that are irrelevant to real fiber flow lines. By applying a technique of a finite element method to the fiber flow lines, deformation calculation is performed. A new trace point is added between trace points when the distance therebetween is great. The velocity of each trace point cause by deformation is calculated, and the position of each trace point is updated. When any trace point in an element is left behind in a die, the left-behind phenomenon is prevented by converting the shape of the element while the crossing of fiber flow lines is prevented. A radius is set for each trace point. The radius of each trace point is adjusted so as to eliminate off-boundary extension and overlap of fiber flow lines.

24 Claims, 22 Drawing Sheets

DIRECTION OF PROCESSING

DIRECTION OF PROCESSING

DIRECTION OF PROCESSING

BEFORE RE-DIVISION       AFTER RE-DIVISION

CONVERSION

METHOD FOR ANALYZING FORGING PROCESS AND MEDIUM STORING PROGRAM FOR EXECUTING THE METHOD

INCORPORATION BY REFERENCE

The disclosure of Japanese Patent Application No. HEI 10-309920 filed on Oct. 30, 1998 and No. HEI 11-223755 filed on Aug. 6, 1999, each including the specification, drawings and abstract, is incorporated herein by reference in its entirety.

BACKGROUND OF THE INVENTION

1. Field of the Invention

The present invention relates to analysis of a forging process of a material and, more specifically, to a technology for analyzing and/or predicting deformation of a workpiece caused due to the forging process performed thereon by setting fiber flow lines in the interior of the workpiece and calculating displacements of the fiber flow lines caused by the forging process. The invention relates particularly to a technology capable of analysis taking three-dimensional information into account.

2. Description of the Related Art

Forging processes, such as pressing or the like, sometimes suffer from defects, such as forging defects, dead metal, buckling or the like, depending on the combination of whether the workability of a material is good and how the material is processed. To analyze such defects, a fiber flow line is conventionally observed. Observation of a fiber flow line makes it possible to identify the type of the defect and detect the condition of friction between the workpiece and a die. In order to observe a fiber flow line, however, it is necessary to prepare a die, forge a material with the die, cut out a sample piece for the observation from the forged material, grind and etch the sample piece, and place it under a microscope. Results of the observation are fed back to the die designing or the production process designing. A single cycle of this procedure of observation and feedback consumes a long period of time, for example, several months. Therefore, the process designing cannot be quickly accomplished.

To avoid consumption of a long time, computer simulation of a forging process is often employed to predict the state of a fiber flow line occurring after the process. In many cases, such a simulation is performed by a finite element method. In a conventional manner of simulation based on the finite element method, a workpiece is divided into many elements by setting a grid mesh in the workpiece, and the displacements of individual element-forming nodes (grid points) are sequentially calculated to simulate the deformation of the entire workpiece.

However, the aforementioned conventional arts have the following problems. That is, the method in which a fiber flow line in an actually processed material is observed consumes an inconveniently long time as mentioned above. Furthermore, the method does not allow observation of material flowage in a cross section of a sample piece perpendicular to the length of the piece because a fiber flow line does not exist in such a section.

The conventional manner of computer simulation of a forging process is not able to provide a result whose fineness exceeds the fineness of the grid mesh set during an initial period of the analysis. This problem becomes remarkable particularly at sites of a workpiece that have high rates of surface area expansion. Furthermore, at a position between nodes, a left-behind phenomenon in which a deformed portion is left behind in a die sometimes occurs. This phenomenon makes it impossible to simulate a precise shape occurring after deformation.

SUMMARY OF THE INVENTION

Accordingly, the invention is intended to solve the aforementioned problems of the conventional technologies for analyzing a forging process. It is an object of the invention to provide a forging process analyzing method that allows simulation of a forging process within a short period of time, and also allows high-precision analysis with respect to a section perpendicular to the length of a workpiece and a site of a great expansion, and further allows display of results of the analysis in a three-dimensional manner, and to provide a medium storing a program for executing the method.

In the forging process analyzing method of the invention, a plurality of trace points for expressing at least one fiber flow line are set in a workpiece that is to be forged by a die. Furthermore, a displacement of each trace point involved in deformation of the workpiece is calculated. At least one post-deformation fiber flow line is expressed in the workpiece by connecting the trace points after displacement.

More specifically, trace points are set in the shape of a workpiece before a process is performed on the workpiece. The trace points provided for expressing fiber flow lines. That is, a bent or curved line obtained by connecting trace points expresses a fiber flow line. Arbitrary fiber flow lines can be set. That is, the fiber flow lines may be lines that match real fiber flow caused by the past processes actually performed on a workpiece or lines based on a simulation of real fiber flow. Furthermore, the fiber flow lines may also be imaginary lines that are irrelevant to real fiber flow. With regard to each trace point, a displacement involved in deformation caused by a process performed on the workpiece is calculated. Normally, this calculation is executed by iterative operation. Then, the post-displacement trace points are connected to form bent or curved lines that express fiber flow lines occurring after the workpiece has been processed.

Based on the post-process fiber flow lines, it is possible to predict whether the workability is good when the workpiece is actually subjected to the forging process. That is, it is possible to predict a possibility of occurrence of defects, such as a forging defect, dead metal, buckling and the like. This forging process analyzing method can be performed through computer processing. The computation time required by the method is only slightly longer than the computation time required when a normal finite element method is employed. Therefore, results of the analysis can be fed back to the die designing and the production process designing in a turn-around time of only one day or less. The forging process analyzing method thus contributes to quick process designing. Furthermore, the method of the invention achieves finer and closer results than a method in which fiber flow lines are formed by using element-forming nodes.

The forging process analyzing method of the invention is intended for the application to an analysis based on a Lagrangian method in which trace points are not fixed in a space but set as mobile points that move together with a workpiece material and the movement of the trace points caused by a workpiece process is tracked. Therefore, it is not essential to place trace points on a surface of a workpiece during the setting of trace points. Trace points belong to the same elements before and after being displaced.

In the forging process analyzing method of the invention, a new trace point may be set between trace points in a portion that has a high rate of expansion caused by deformation. That is, when calculation of a displacement of each trace point finds that the distance between post-displacement trace points has become equal to or greater than a certain value, a new trace point is set between those trace points. Then, the subsequent calculating process is performed. Therefore, it becomes possible to perform fine and close analysis even at a site of a high rate of expansion caused by the workpiece process (typically interpreted as a high rate of expansion of surface area).

The additional setting of a new trace point may be performed in the following manner. That is, a distance between adjacent trace points present on a fiber flow line is compared with a predetermined critical value. When the distance between the adjacent trace points exceeds the critical value, a new trace point is set. This manner of setting a new trace point prevents the distance between trace points from exceeding the critical value even at a site of expansion caused by deformation. Therefore, it becomes possible to perform fine and close analysis even at a site of a high expansion rate.

Furthermore, in the forging process analyzing method of the invention, when there is a trace point that is to be left behind in a die due to deformation, an element containing the trace point may be converted into a correction element in which an element side extending in a shape of the die is replaced by a line expressing the shape of the die. Through conversion of the element, positions of all trace points present in the element that contains the trace point that would otherwise be left behind can be corrected by an interpolating process. This processing manner makes it possible to perform high-precision analysis even in a portion where a normal finite element method would cause a trace point to be left behind in the die or cause fiber flow lines to cross each other, and therefore would suffer form a remarkable reduction of analysis precision.

Prevention of such a left-behind phenomenon may be performed as follows. When a die shape-expressing line extends in an outermost peripheral element of a workpiece, it is determined that a trace point contained in the outermost peripheral element is likely to be left behind in the die. Then, a process for preventing the left-behind phenomenon is performed with respect to the trace points contained in the element. That is, the aforementioned conversion is performed on the element, and the positions of all the trace points present in the element are corrected.

In the forging process analyzing method of the invention, it is also possible to set trace points so as to express fiber flow lines in a section that intersects with the length of a workpiece and, in particular, a section perpendicular to the length of the workpiece. In the case of a material prepared in a normal shape, such as a billet or a platy material or the like, the aforementioned section does not have fiber flow in reality. Therefore, the behavior of deformation in such a section cannot easily be analyzed by a method in which a test sample is polished and etched and then observed. However, since the forging process analyzing method of the invention is able to analyze imaginary fiber flow lines, the method can analyze fiber flow lines in a section intersecting with the length of a workpiece. That is, the method can also analyze fiber flow lines expressed by trace points set in the aforementioned manner. Therefore, it becomes possible to predict a condition of migration of the material in a section that interests with the length of the workpiece.

Furthermore, in the forging process analyzing method of the invention, a fiber flow line having a thickness may be expressed by providing post-displacement trace points with radii. As a result, each fiber flow line is expressed not as a mere point but as a finite area even during the observation of a section that intersects with the post-deformation fiber flow lines. Therefore, when three-dimensional consideration is to be performed on results of the analysis, the behavior of fiber flow lines can easily be understood in an arbitrarily selected section. This technique is particularly useful when trace points are set by simulating real fiber flow lines.

When such a three-dimensional analysis is to be performed, the radius of a trace point should be adjusted because after the workpiece is deformed, a trace point may possibly be located close to a surface of the workpiece or may be located close to another trace point. When in such cases, equal radii are provided for all the trace points, a fiber flow line containing a trace point adjacent to a surface of the workpiece will likely extend out of the boundary of the workpiece in the former case. In the latter case, adjacent fiber flow lines will likely overlap each other. Neither the off-boundary extension nor the overlap of fiber flow lines can occur in reality since fiber flow lines do not have a thickness in a real workpiece.

Therefore, when there is a fiber flow line extending off the boundary of a workpiece, the radius of the fiber flow line should be adjusted so that the fiber flow line is contained inside the boundary of the workpiece. When fiber flow lines overlap each other, the radius adjustment should be performed so that the overlap is eliminated. In either case, the radius adjustment is performed in the reducing direction. The radius adjustment for the aforementioned purposes may be applied collectively to all the trace points, or may also be applied individually to only the trace points having a specific problem as mentioned above. It should be noted that the latter manner of radius adjustment is more advantageous because larger radii of fiber flow lines make an easier-to-see display of results of the analysis.

When the trace points are provided with radii in this invention, it is useful to provide a display picture in which the interior of each fiber flow line is filled in in a section of the workpiece after the workpiece has been deformed. In such a display, the condition of congregation of fiber flow lines can be grasped based on the degree of sparsity or density of the filled-in portions. Furthermore, based on the shape of a filled-in portion (whether it is circular or elliptical), the intersecting angle of the fiber flow line to which the filled-in portion belongs with respect to the sectional face can be estimated. Therefore, it becomes possible to perform further detailed or three-dimensional consideration on results of the analysis.

The mechanically readable medium of the invention stores a program for causing a computer to execute the above-described procedures of the forging process analyzing method of the invention. Using the mechanically readable medium, it becomes possible to cause a computer to execute the forging process analyzing method of the invention.

BRIEF DESCRIPTION OF THE DRAWINGS

The foregoing and further objects, features and advantages of the present invention will become apparent from the following description of preferred embodiments with reference to the accompanying drawings, wherein like numerals are used to represent like elements and wherein:

FIG. 25 illustrates a display in which sections of fiber flow lines each having a sectional area are filled in;

DETAILED DESCRIPTION OF PREFERRED EMBODIMENT

Figure 1:
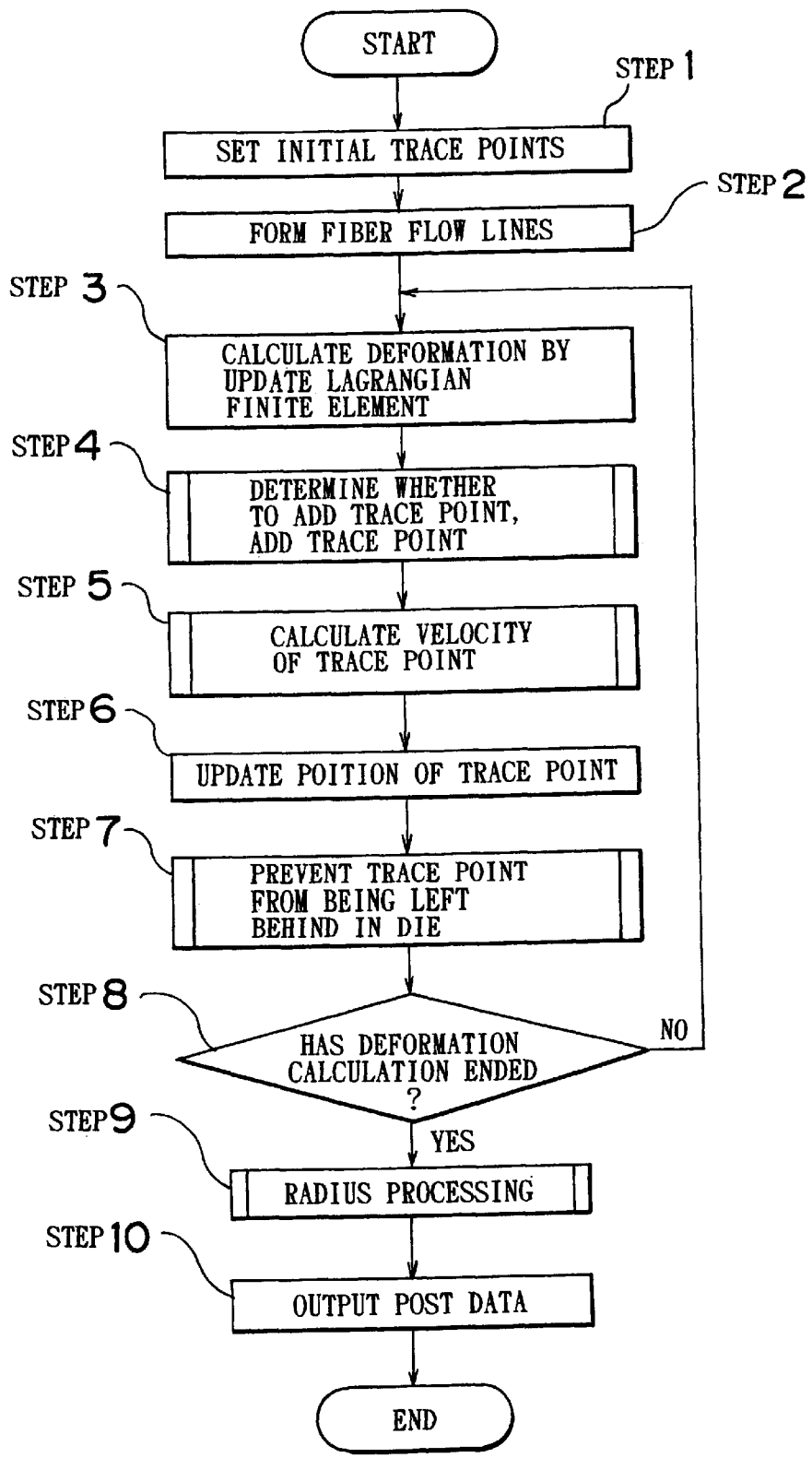
FIG. 1 is a flowchart illustrating a procedure of a forging process analyzing method according to an embodiment of the invention.

A preferred embodiment of the present invention will be described in detail hereinafter with reference to the accompanying drawings. In a forging process analyzing method according to this embodiment, analysis is performed by a computer, such as a personal computer, a workstation or the like, by a procedure as illustrated by the flowchart of FIG. 1. A program needed to cause the computer to execute necessary processes is recorded in a medium, for example, a floppy disk, a compact disk or the like. The computer reads the program recorded on the medium, and executes processes described below.

In steps 1 and 2, the computer sets many trace points in the interior of a workpiece of steel or the like. In setting trace points, the computer take into account the initial shape of the workpiece, the target shape, condition of friction against a tools, and other information. The group of trace points thus set are used to express a fiber flow line of the workpiece. That is, straight line segments and bent lines passing through the trace points express a fiber flow line. The fiber flow line thus expressed may be a simulation of a fiber flow line that actually exits due to the processing to which the workpiece has been subjected or may be a virtual line irrelevant to actual fiber flow. It should be noted that coordinates (value in an entire coordinate system) of each trace point are recorded.

Figure 2:
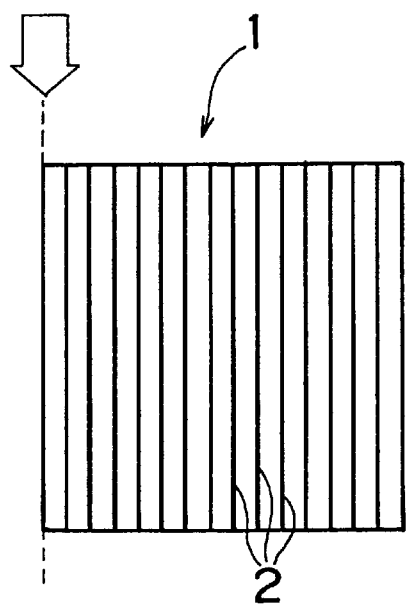
FIG. 2 is an example illustration of fiber flow lines initially set in a workpiece.
Figure 3:
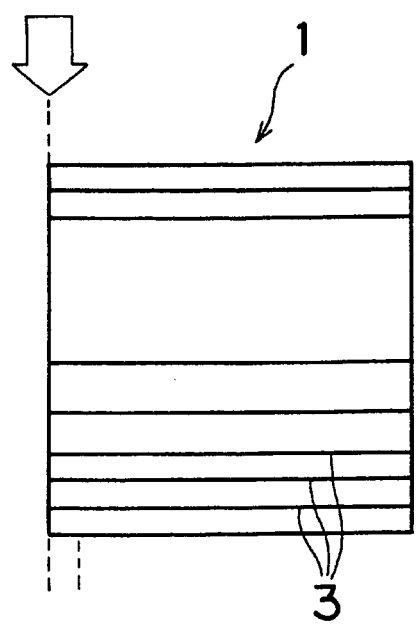
FIG. 3 is another example illustration of fiber flow lines initially set in a workpiece.
Figure 4:
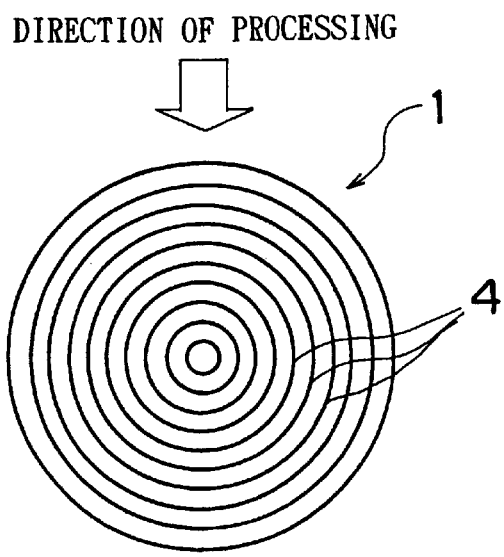
FIG. 4 is still another example illustration of fiber flow lines initially set in a workpiece.
Figure 5:
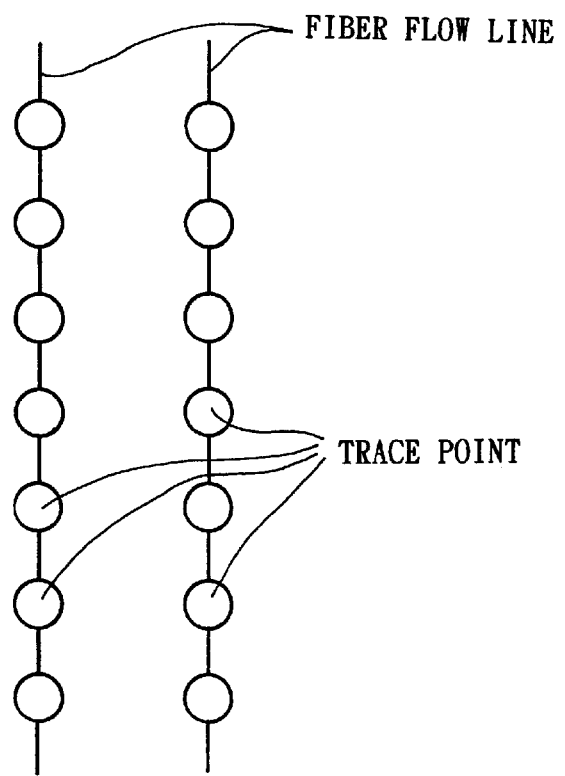
FIG. 5 is an illustration of trace points initially set in a workpiece and fiber flow lines expressed by the trace points.

For example, in a case where a cylindrical billet workpiece is subjected to a processing in a direction of the length thereof and a direction perpendicular to the direction of length, a group of trace points can be set so as to express fiber flow lines as shown in FIGS. 2, 3 or 4. In the example case shown in FIG. 2, fiber flow lines 2 expressed by trace points extend in directions perpendicular to the directions of the length (right-to-left directions in FIG. 2) of the cylindrical billet 1, that is, in directions parallel to the direction of processing. In the example shown in FIG. 3, fiber flow lines 3 expressed by trace points extend in directions parallel to the length of the cylindrical billet 1, that is, in directions perpendicular to a direction of processing. In the example shown in FIG. 4, fiber flow lines 4 expressed by trace points extend in a section perpendicular to the length. In these example cases, many trace points exist on fiber flow lines as shown in FIG. 5. That is, straight lines (or bent lines or curved lines) connecting the set trace points express the fiber flow lines. The fiber flow lines 4 shown in FIG. 4 are virtual fiber flow lines irrelevant to actual fiber flow in the cylindrical billet.

Figure 6:
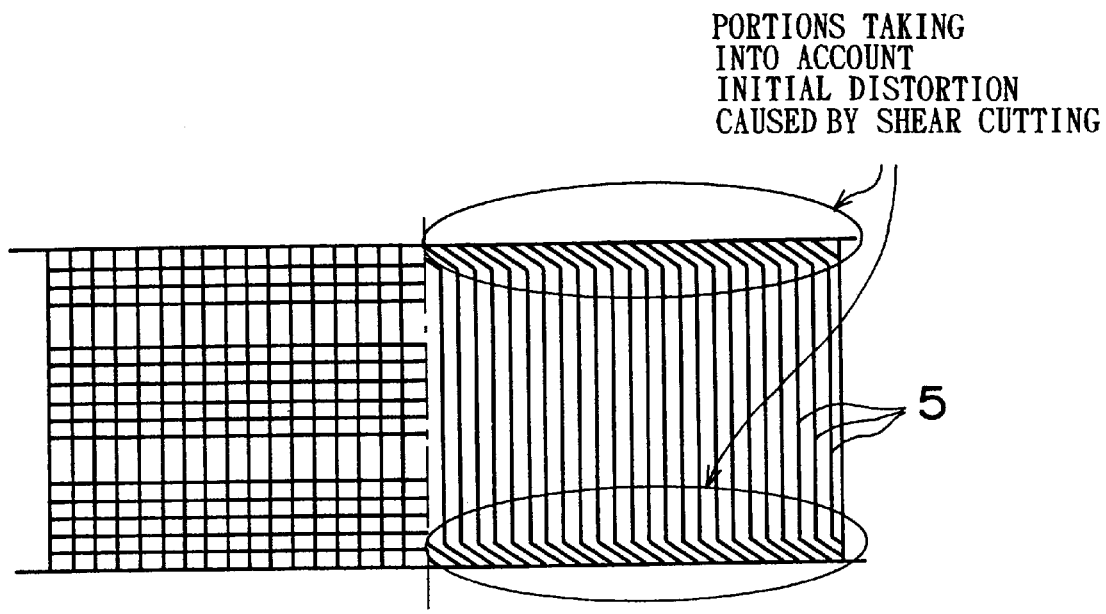
FIG. 6 is an example illustration of fiber flow lines set taking into account the initial distortion in a workpiece.

Distortion (initial distortion) of fiber flow caused in a workpiece by the processing that the workpiece has received may be taken into account in setting fiber flow lines. An example case of such setting is shown in FIG. 6, in which the workpiece is a small piece cut out from a material bulk by shear cutting. In regions adjacent to upper and lower end faces shown in a right-side half of the view of FIG. 6, fiber flow lines 5 are set taking into account distortion caused by shear cutting. That is, in the right-side half in FIG. 6, fiber flow lines 5 mainly extend in parallel to the thickness of the workpiece, and are bent near the upper and lower end faces. Based on the bent angle of the fiber flow lines and the length of bent portions, initial distortion can be arbitrarily set.

Figure 7:
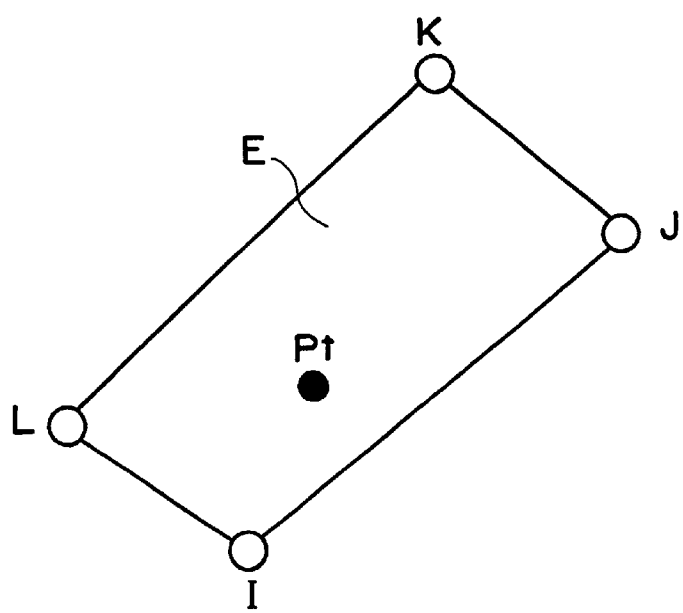
FIG. 7 illustrates the setting of a finite element in a workpiece.

In step 3, the computer calculates deformation caused by a forging process. This calculation is performed by a Lagrangian finite element method. That is, the entire workpiece is subjected to an update Lagrangian finite element method. More specifically, the entire workpiece is subjected to generally-termed meshing, in which the workpiece is divided into many finite elements defined by nodes. As a result, each trace point is contained in a finite element as shown in FIG. 7. In FIG. 7, a trace point Pt is contained in a finite element E defined by nodes I, J, K, L. Shape functions are determined for the individual finite elements. Rates of displacement due to deformation are determined for the individual nodes.

Subsequently in step 4, the computer performs an operation of determining whether to add a trace point and accordingly adding a trace point. This operation is performed as illustrated by the flowchart of FIG. 8.

Figure 8:
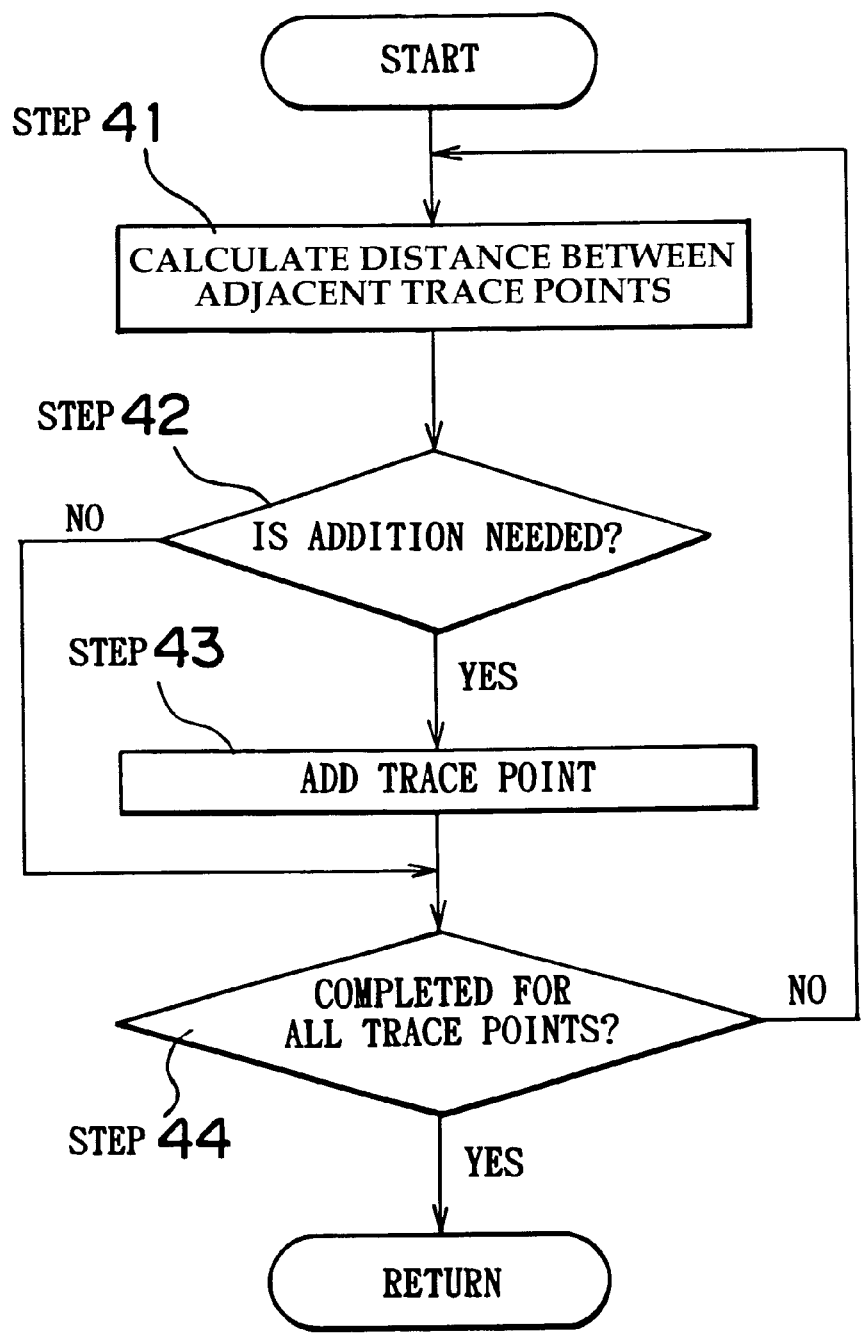
FIG. 8 is a flowchart illustrating in detail a process of adding a new trace point.

In step 41 in FIG. 8, the computer calculates distances between adjacent trace points. This calculation is performed on the basis of the recorded coordinates of each trace point. The distances calculated in this step is distances between adjacent trace points on the fiber flow lines.

Subsequently in step 42, the computer determines, based on the distance between the adjacent trace points calculated in step 41, whether there is a need to add a new trace point between those trace points. When the distance between the adjacent trace points is greater than a predetermined critical value, it is determined that there is a need to add a new trace point (YES in step 42). When a further expansion is caused by deformation at such a site (where the distance between adjacent trace points is great), the distance between the trace points becomes excessively great, so that the analysis precision decreases. Such an undesired event can be prevented by adding a new trace point. When the inter-trace point distance is equal to or less than the critical value, it is determined that there is no need to add a new trace point (NO in step 42).

Figure 9:
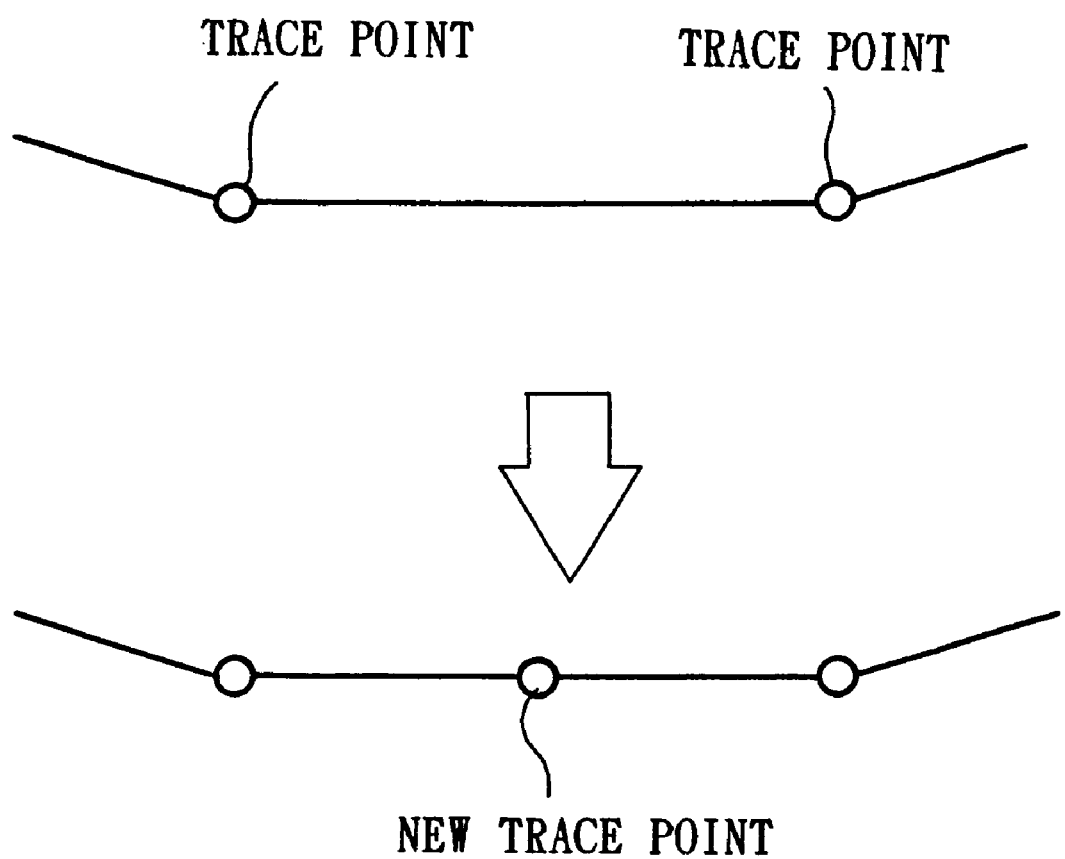
FIG. 9 is a schematic illustration of a situation in which a new trace point is added.

When the determination in step 42 is affirmative, a new trace point is added between the adjacent trace points (see FIG. 9) in step 43. As a result, the inter-trace point distance is controlled within the critical value, so that a certain analysis precision is maintained. When the determination in step 42 is negative, step 43 is bypassed.

Subsequently in step 44, it is determined whether the above-described processing is completed for all the trace points. When there is a trace point that has not been subjected to the processing (NO in step 44), the computer returns to step 41 to repeat the processing. When the processing is completed for all the trace points (YES in step 44), the computer goes back to the main routine illustrated in FIG. 1.

Subsequently in step 5 in the main flowchart of FIG. 1, the computer calculates a velocity of each trace point. This processing is performed as illustrated by the flowchart of FIG. 10.

Figure 10:
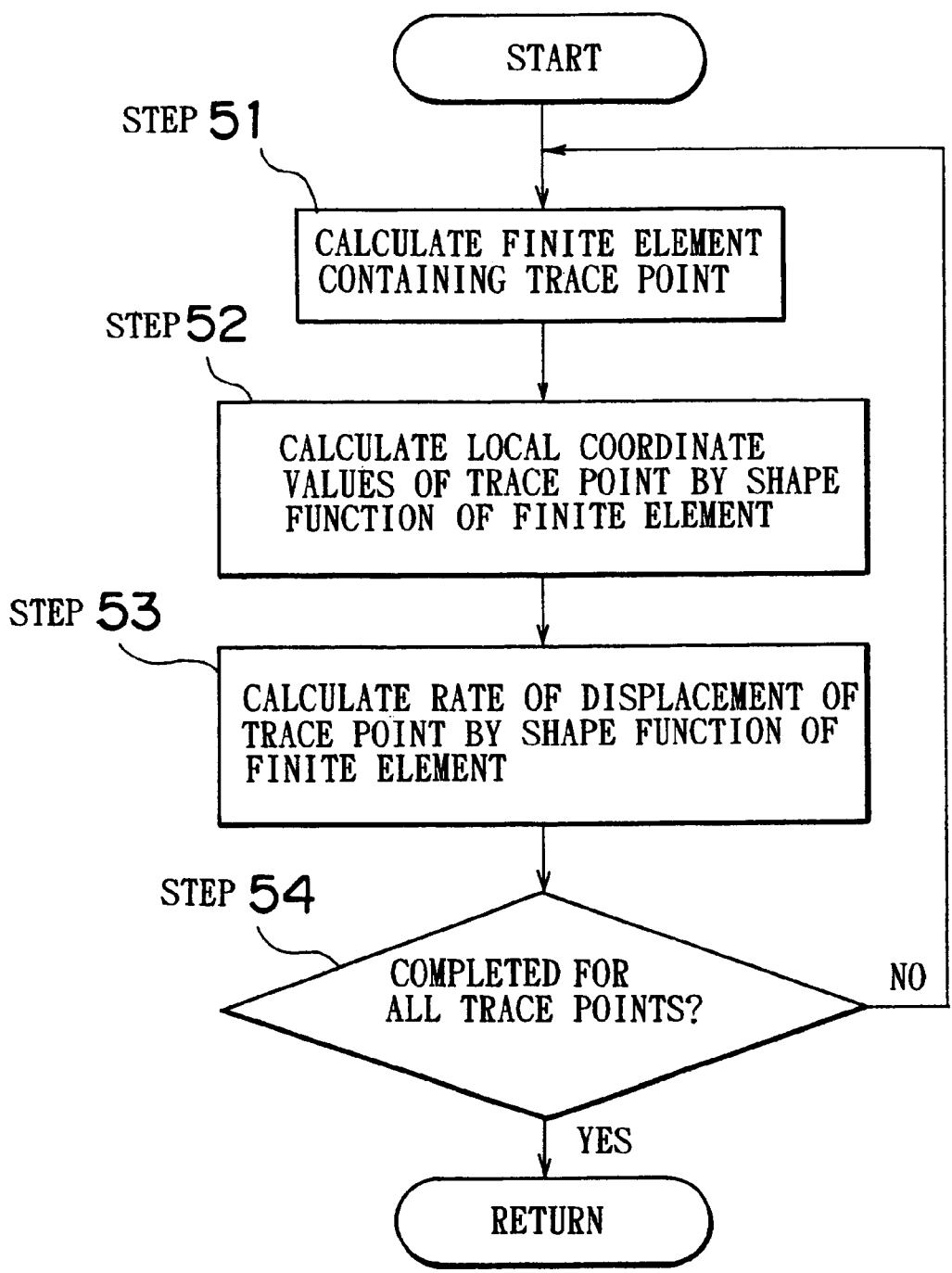
FIG. 10 is a flowchart illustrating in detail a process of calculating a rate of displacement of each trace point.

In step 51 in FIG. 10, the computer determines, with respect to a certain trace point, which one of the finite elements contains the trace point. This computation is performed based on the coordinates of the trace point and the coordinates of the nodes of a finite element. In an example case shown in FIG. 7, a trace point Pt is contained in a finite element E defined by nodes I, J, K, L.

Figure 11:
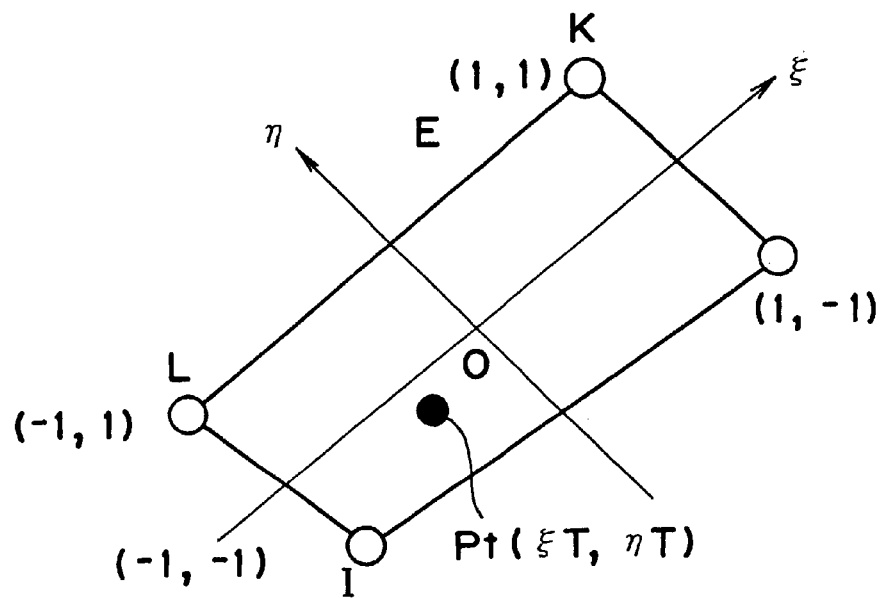
FIG. 11 is a schematic diagram illustrating calculation of local coordinates in a finite element.

Subsequently in step 52, the computer calculates the values of local coordinates of that trace point in the finite element. This calculation is based on the coordinate values of the nodes and the trace point in the entire coordinate system (r, z) and the shape function of the finite element, which are already known. A manner of the calculation will be described with regard to the trace point Pt shown in FIG. 7. The local coordinate system $(\xi, \eta)$ in the finite element E is defined by coordinate axes $\xi, \eta$ each of which divides the finite element E into substantially equal halves with respect to a corresponding one of two directions, as indicated in FIG. 11. In this coordinate system, the coordinate values of the nodes I, J, K, L are (−1, −1), (1, −1), (1, 1), (−1, 1), respectively. Therefore, the coordinate values $\xi_T, \eta_T$ of the trace point Pt are both within the range of −1 to 1. The coordinate values $\xi_T, \eta_T$, of the trace point Pt can be determined by converting the coordinate values $(r_T, z_T)$ of the trace point Pt in the entire coordinate system through the use of the coordinate values of the nodes in the entire coordinate system.

Subsequently in step 53, the computer calculates the rate of displacement (velocity) of the trace point Pt caused by deformation. As isoparametric elements for the calculation, the computer uses the local coordinate values $(\xi_T, \eta_T)$ of the trace point Pt, the velocities $(u_I, v_I), (u_J, v_J), (u_K, v_K), (u_L, v_L)$ of the nodes I, J, K, L, and the shape function N. The velocity of each node has been determined in step 3. Therefore, the velocity $(u_T, v_T)$ of the trace point Pt can be determined as follows:

$$u_T = \Sigma(N_M \times u_M)$$

$$v_T = \Sigma(N_M \times v_M)$$

Figure 12:
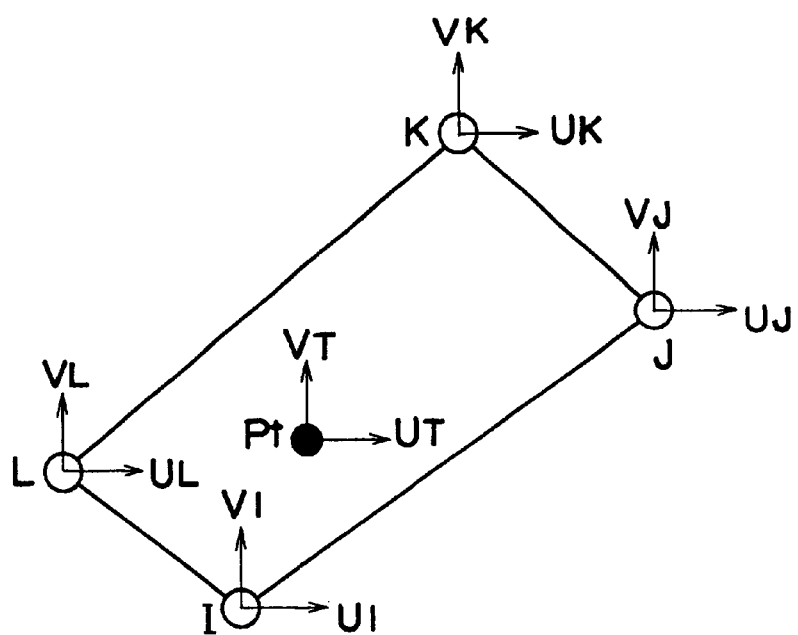
FIG. 12 is a schematic diagram illustrating calculation of a rate of displacement of a trace point.

In the equations, the affix "$_M$" represents the nodes I, J, K, L. The symbol "$\Sigma$" indicates that the multiplication products of the shape function N and the velocity component u (or v) for the four nodes are summed. FIG. 12 indicates velocity components (u, v) of the trace point Pt and the nodes I, J, K, L.

In step 54, the computer determines whether the above-described processing is completed for all the trace points. When there is a trace point that has not been subjected to the processing (NO in step 54), the process returns to step 51, where another trace point is set as an object trace point and the processing for the object trace point is performed. When the processing is completed for all the trace points (YES in step 54), the process returns to the main routine illustrated in FIG. 1.

In step 6 in the main flowchart of FIG. 1, the position of each trace point is updated. That is, the computer determines coordinate values of each trace point Pt after displacement on the basis of the velocity $(u_T, v_T)$ of the trace point Pt calculated in step 5 (FIG. 10). The coordinate values of each trace point Pt are overwritten by the post-displacement values. The coordinate values of the nodes are also overwritten on the basis of their respective velocities.

Figure 13:
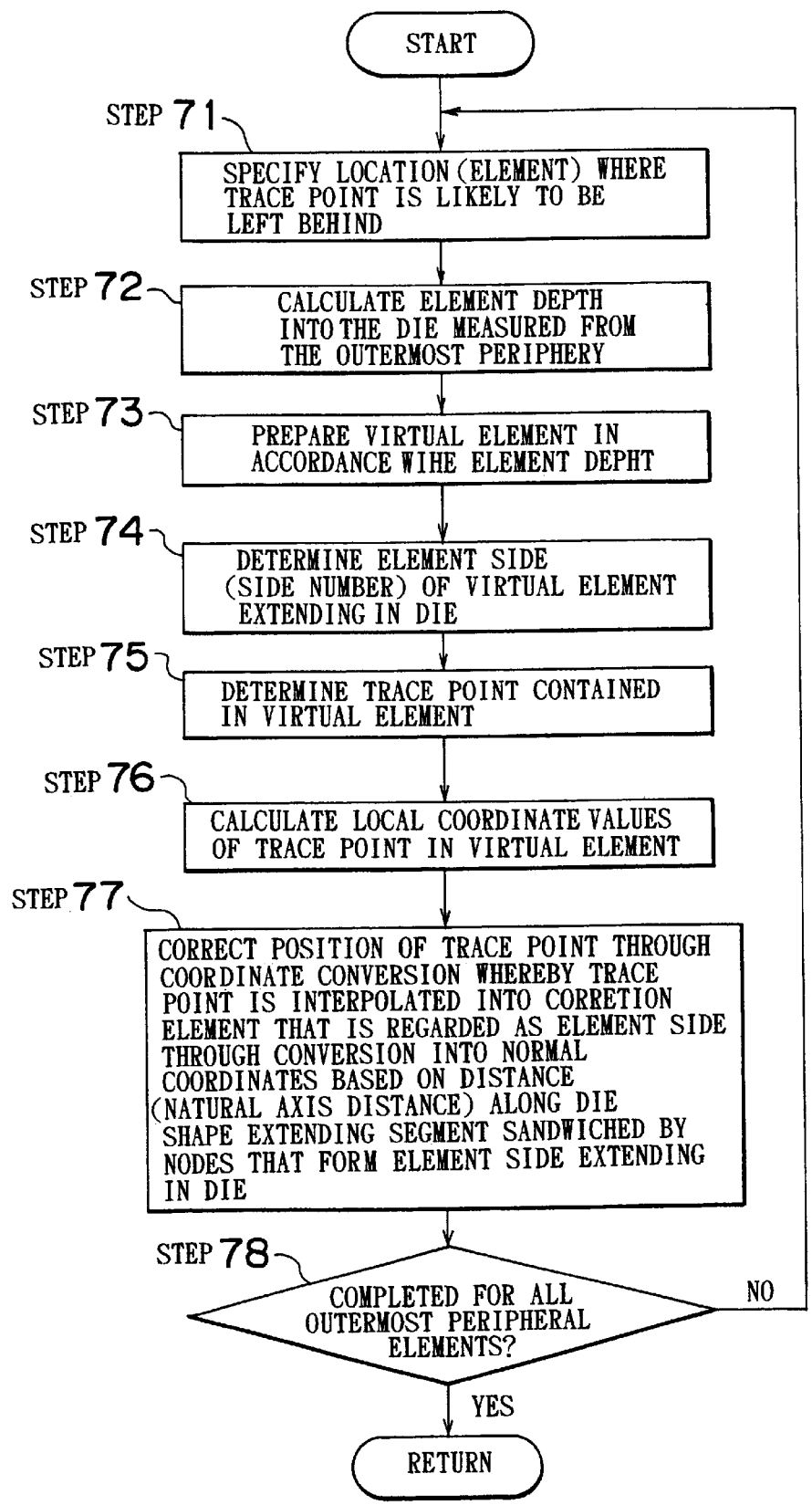
FIG. 13 is a flowchart illustrating in detail a process of preventing a trace point from being left behind in a die.
Figure 14:
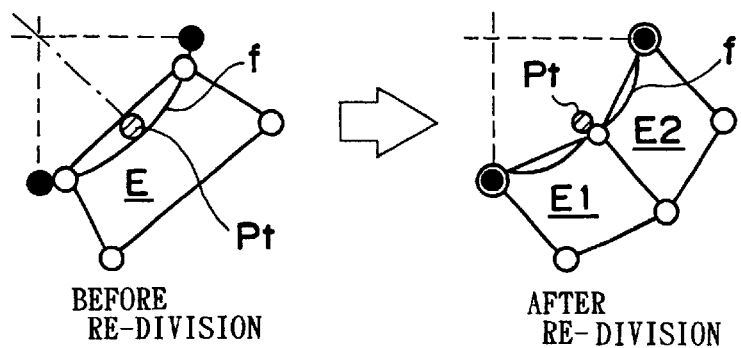
FIG. 14 is a schematic diagram illustrating a problem caused by re-division of an element.

Subsequently in step 7, the computer executes a processing for preventing the phenomenon in which a trace point is left behind in a die. This processing is necessary for the following reasons. Due to the position update in step 6, a finite element may be re-divided in the next cycle of the routine. When that happens, there can occur a case where a trace point Pt is contained in an old finite element E before re-division, but is not contained either one of the new finite elements E1, E2 after re-division. When the analysis is simply continued, the trace point Pt is left out of the shape of the workpiece and therefore left behind inside the shape of a die. This phenomenon cannot occur with a real workpiece. Therefore, this phenomenon in the simulation means a remarkable reduction of the analysis precision. Consequently, the left-behind phenomenon needs to be prevented in order to achieve a high analysis precision. The processing for preventing the phenomenon is executed as illustrated by the flowchart of FIG. 13. In the illustration FIG. 14, a curve f indicates a die segment.

Figure 15:
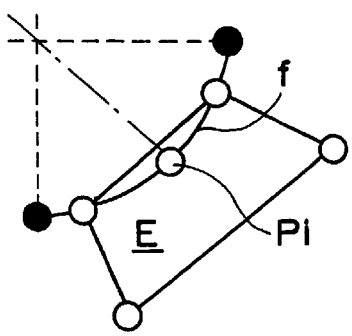
FIG. 15 is a schematic diagram illustrating identification of an element in which the left-behind phenomenon occurs.
Figure 16:
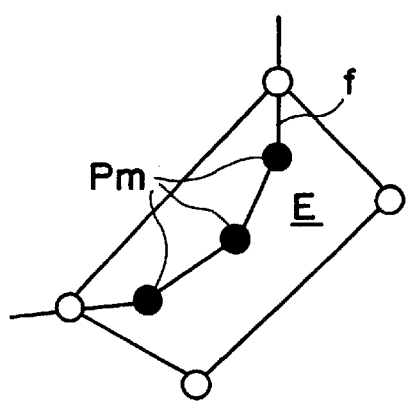
FIG. 16 is a schematic diagram illustrating identification of an element in which the left-behind phenomenon occurs.

In step 71, the computer executes a processing for specifying a location at which there is a possibility of leaving a trace point behind. This processing is based on whether the shape of a die extends into an object finite element. For example, when a die segment has a convex arc shape, there may occur a case where a virtual evaluation point Pi set on the die segment f enters the finite element E, as shown in FIG. 15. In such a case, it is determined that the finite element E is a location where a trace point is likely to be left behind. Furthermore, in a case as shown in FIG. 16 where a die segment f is expressed by bent lines connecting points Pm that express the shape of a die and where the die shape-expressing points Pm are located within a finite element E, it is also determined that the finite element E is a location where a trace point is likely to be left behind.

Figure 17:
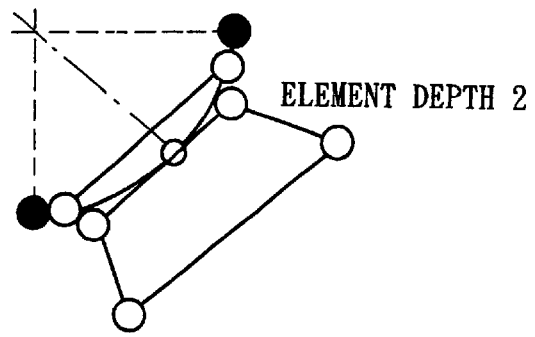
FIG. 17 is a schematic diagram illustrating calculation of an element depth extending into a die.

Subsequently in step 72, the computer calculates a protrusion depth into a die with respect to a finite element that has been found to have a possibility of leaving a trace point behind. That is, the computer calculates a depth of the element measured from an outermost periphery protruded into the die at the location (element) as shown in FIG. 17.

Figure 18:
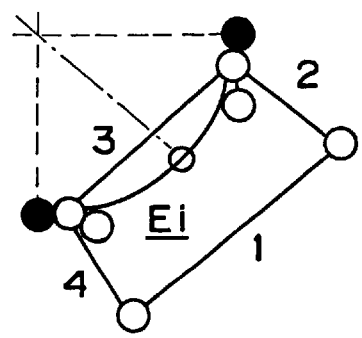
FIG. 18 is a schematic illustration of a situation in which a virtual element is prepared in accordance with the element depth extending into a die.

In steps 73 and 74, the computer prepares a virtual element in accordance with the calculated element depth. That is, in accordance with the element depth, the computer forms a virtual element Ei based on outermost nodes and innermost nodes, as shown in FIG. 18. Subsequently, the computer determines a side (the number thereof) of the virtual element Ei extending in the die. The sides of each element are line segments connecting between nodes that define the virtual element. In the case shown in FIG. 18, the number of the side of the element extending in the die is "3".

Subsequently in step 75, the computer determines a trace point that is contained in the virtual element. The trace points contained in the virtual element are relatively highly likely to be left behind in the die. Therefore, a trace point contained in the virtual element becomes a subject of the below-described processings of steps 76, 77. The trace points not contained in the virtual element can be said to have substantially no possibility of being left behind in the die. Hereinafter, trace points contained in a virtual element will be referred to as "correction trace points".

In step 76, the computer calculates coordinate values of a correction trace point in the local coordinate system ($\xi_I, \eta_I$) within the virtual element. This calculation is performed by a technique similar to that used in step 52 (see FIG. 11). That is, local coordinate values of a correction trace point are determined by converting the coordinate values of the correction trace point in the entire coordinate system (r, z) through the use of the coordinate values of the nodes in the entire coordinate system. There is a case where a plurality of correction trace points exist on a single fiber flow line and belong to different virtual elements. In such a case, it is recommendable to perform this calculation by grouping correction trace points separately for each virtual element.

Figure 19:
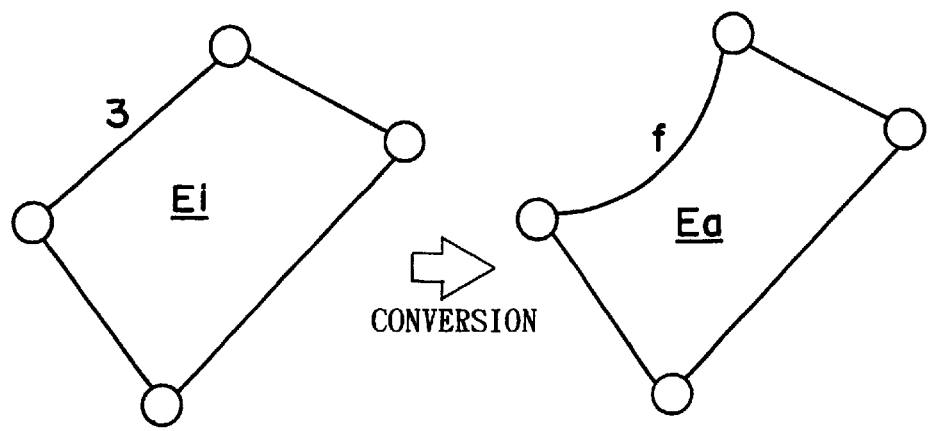
FIG. 19 illustrates conversion of a virtual element.
Figure 20:
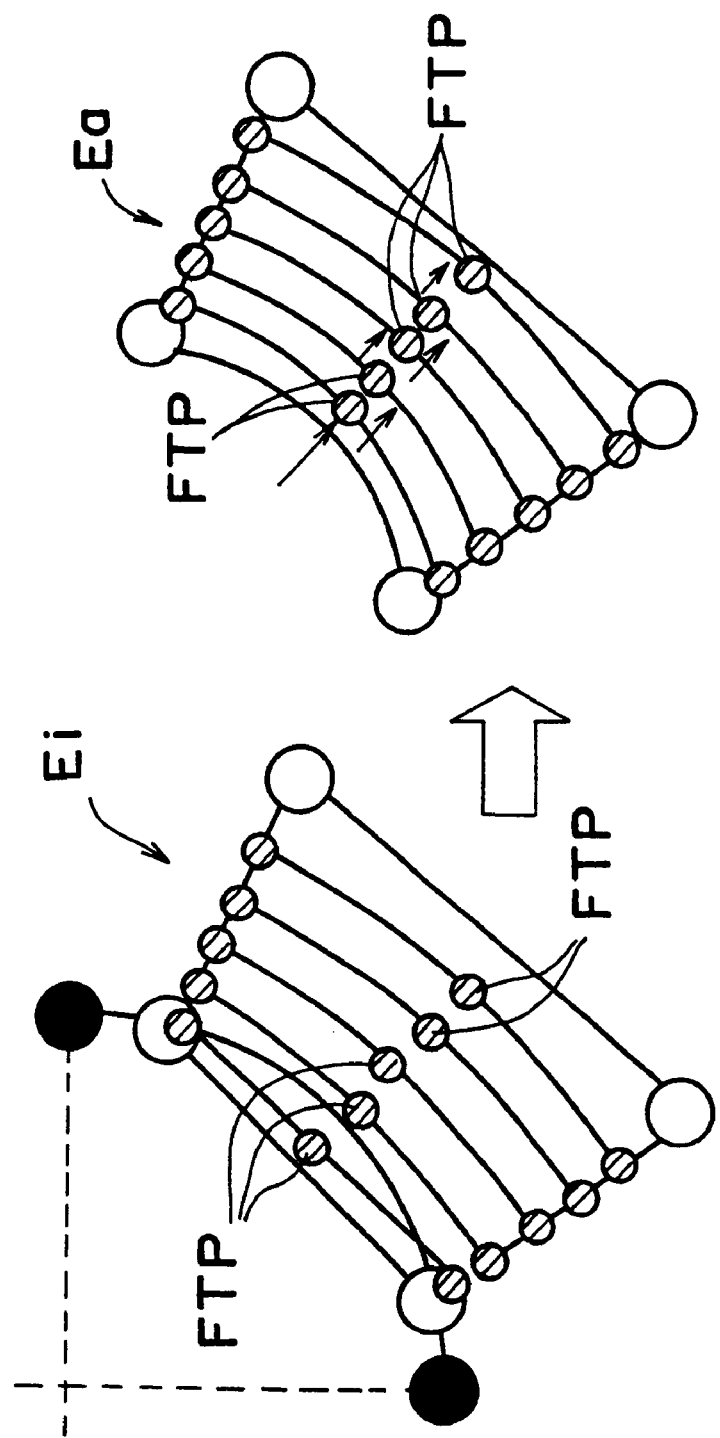
FIG. 20 illustrates position correction of trace points involved in the conversion of a virtual element.

Subsequently in step 77, the computer executes a processing of correcting the position of the correction trace point. This processing is performed as follows. Of the die segment, a portion sandwiched by the opposite end nodes of the element side extending in the die (side 3 in FIG. 18) is first considered. The computer performs coordinate conversion wherein correction trace points are interpolated into a correction element in which an element side is set through the conversion into normal coordinates based on the distance along the sandwiched portion (natural axis distance). That is, the computer assumes a correction element Ea obtained by replacing the element side 3 of the virtual element Ei with a shape expressing line f of the die segment, as shown in FIG. 19. The computer then transfers all the points present in the virtual element Ei into the correction element Ea by one-to-one mapping. Through this processing, the correction trace points in the virtual element Ei (indicated by FTP in FIG. 20) are subjected to position correction in which the points are shifted downwardly rightward as illustrated in FIG. 20. The direction of the shift corresponds to the direction of the $\eta$-axis in the local coordinate system. This position correction prevents a trace point from being left behind.

It can be seen from FIG. 20 that the trace points subjected to the position correction are not only the trace points actually located within the die but all the trace points present in the virtual element. Therefore, it does not happen that only one of adjacent fiber flow lines in a virtual element is subjected to the position correction. This manner of position correction also prevents a line cross phenomenon in which fiber flow lines intersect each other. Since the line cross phenomenon never occurs in real workpieces, it can be said that prevention of the line cross phenomenon in simulation improves the analysis precision.

Furthermore, since the prevention of the left-behind phenomenon is accomplished by the interpolating operation following the position update of step 6, it is not necessary to perform deformation calculation again by going one cycle back. Therefore, an unreasonably increased calculation time is prevented.

The processing from step 71 to step 77 is executed for the individual finite elements located at an outermost periphery of the workpiece. After the processing is completed for all the outermost peripheral elements, that is, when the determination in step 78 becomes affirmative, the process returns to the main routine illustrated in FIG. 1.

Figure 21:
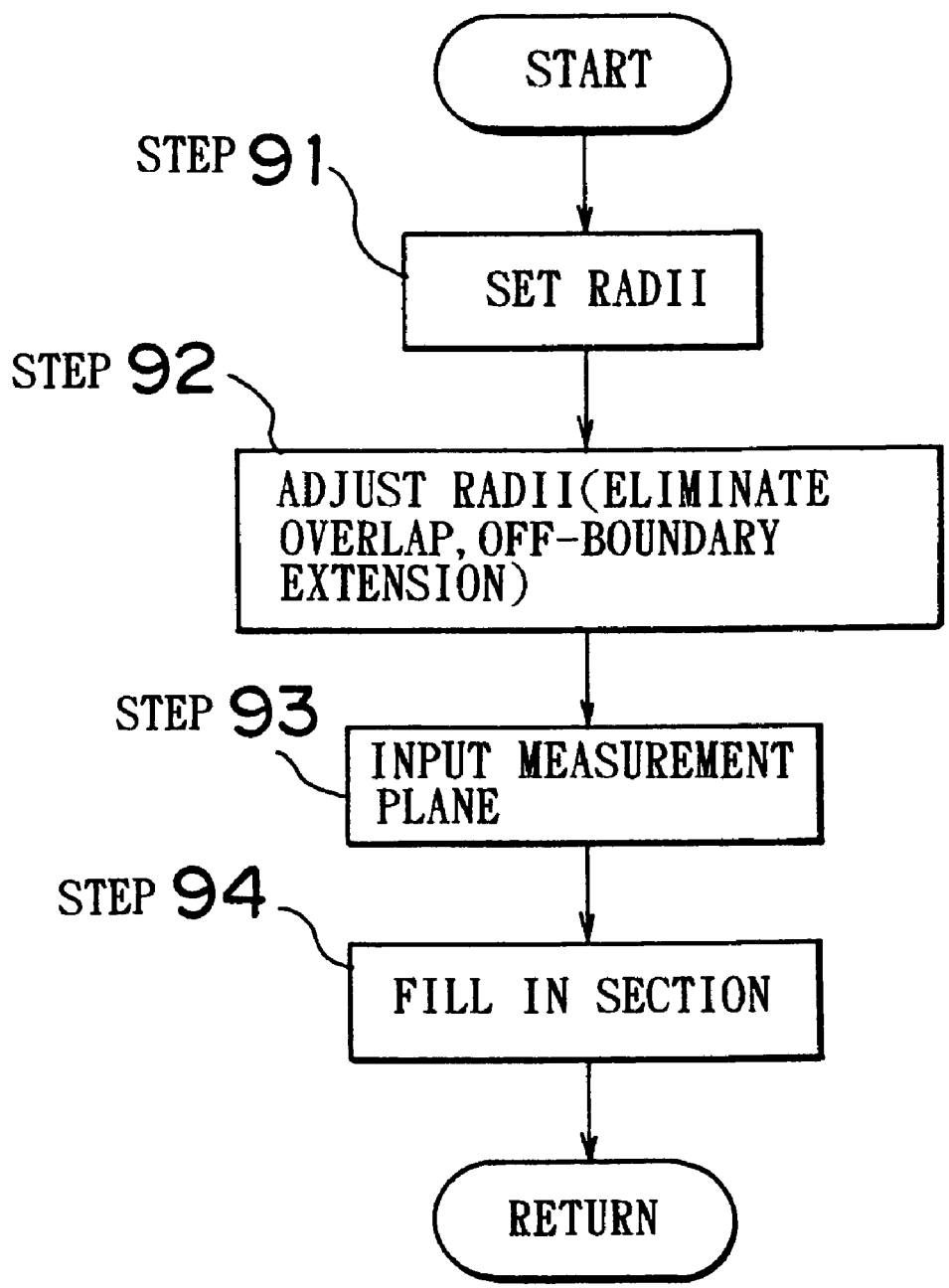
FIG. 21 is a flowchart illustrating a content of a radius processing performed after deformation calculation.

Subsequently in step 8 in the main routine illustrated in FIG. 1, the computer determines whether all the cycles of deformation calculation have ended. When the cycles have not ended (NO in step 8), the computer returns to step 3 in order to repeat the above-described process. When all the cycles of deformation calculation have ended (YES in step 8), the computer proceeds to step 9. In step 9, the computer executes a radius processing for three-dimensional evaluation of results of the analysis. The radius processing is executed as illustrated by the flowchart of FIG. 21.

Figure 22:
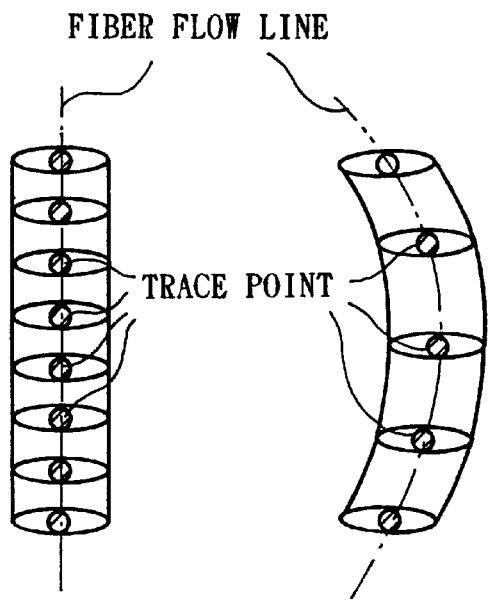
FIG. 22 illustrates a state in which trace points are provided with radii.

In step 91, the computer sets a radius for each trace point. In a case shown in FIG. 22, equal radii are set around the individual trace points on a fiber flow line. The purpose of the radius setting is to provide the fiber flow line with a thickness such that the fiber flow line can be visually identified even during observation of a plane that intersects the fiber flow line occurring after deformation by workpiece processing.

Figure 23:
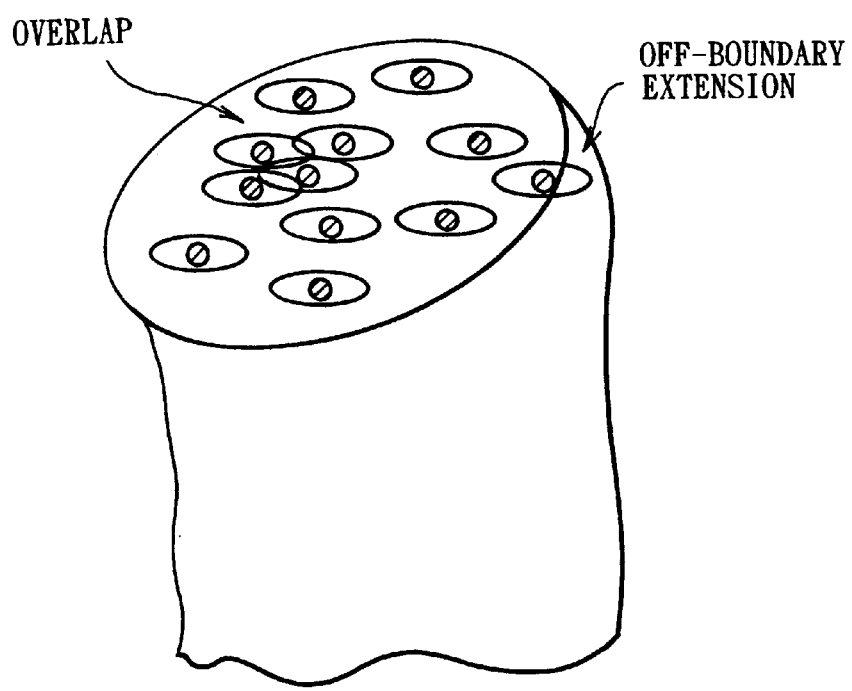
FIG. 23 illustrates the need for radius control.

Subsequently in step 92, the radius of each trace point is adjusted. The purpose of the adjustment is to eliminate overlap between fiber flow lines having a thickness or extension of a thick fiber flow line beyond the boundary of the workpiece. More specifically, the distribution of fiber flow lines in a deformed workpiece is not altogether uniform, so that mere provision of a radius around each trace point results in overlap between fiber flow lines or extension of a fiber flow line off the workpiece as shown in FIG. 23. The processing of preventing the in-die left-behind phenomenon in step 7 eliminates intersection and off-boundary extension of only fiber flow lines having no thickness.

Therefore, the provision of a radius in step 91 may possibly cause off-boundary extension or overlap of fiber flow lines. A fiber flow line provided with a thickness can be considered to represent a bundle of fiber flow lines in the workpiece. Since such overlap or off-boundary extension never occurs in real workpieces, it is necessary to eliminate overlap or off-boundary extension of fiber flow lines provided with a thickness in simulation.

Figure 24:
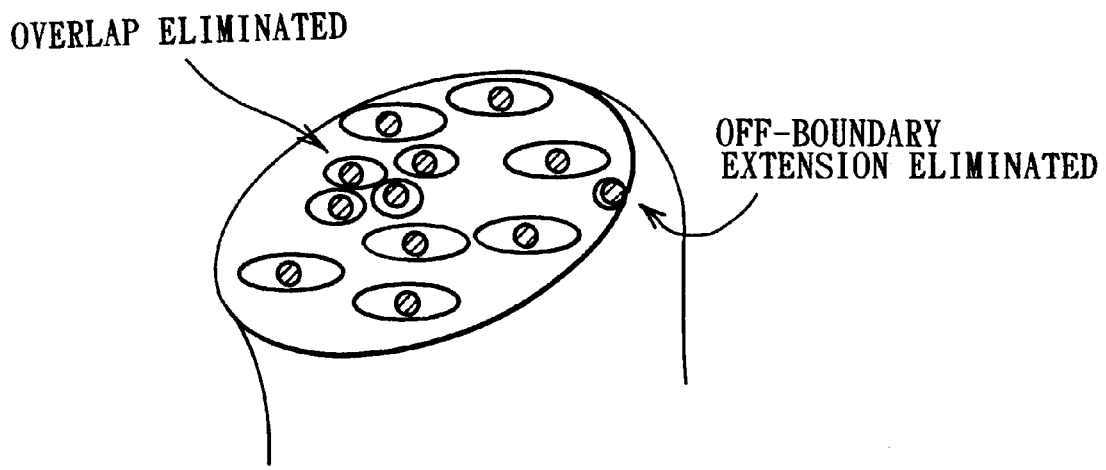
FIG. 24 illustrates a state in which off-boundary extension and overlap of fiber flow lines are eliminated by radius control.

In the radius adjustment in step 92, therefore, the radius about each trace point concerned with overlap or off-boundary extension is reduced to such a level that the overlap or off-boundary extension is eliminated. FIG. 24 shows a state resulting from the radius adjustment performed in the state shown in FIG. 23. In the state shown in FIG. 24, only the trace points concerned with overlap or off-boundary extension have been subjected to radius reduction and the other trace points maintain the original radius. This is advantageous because larger radii of the trace points allow an easier-to-see picture for the later display. It is also possible to adopt a method in which all the trace points are subjected to uniform radius reduction, when only the distribution of fiber flow lines is a critical issue. It is also possible to adopt a method in which the trace points not concerned with overlap or off-boundary extension are subjected to radius expansion within such an extent that neither overlap nor off-boundary extension occurs. Through this method, the sparsity or density of the distribution of fiber flow lines is expressed by the thickness of the fiber flow lines.

In step 93, a measurement plane is inputted by an operating person. The measurement plane is a virtual sectional face of the workpiece, and is a plane for observing the distribution of fiber flow lines each having an adjusted thickness. The plane selected as a measurement plane may extend in an arbitrary direction regardless of the direction of the fiber flow lines in the workpiece after deformation. The plane that can be selected is not only a plane containing therein a fiber flow line but also a plane intersecting a fiber flow line.

Figure 25:
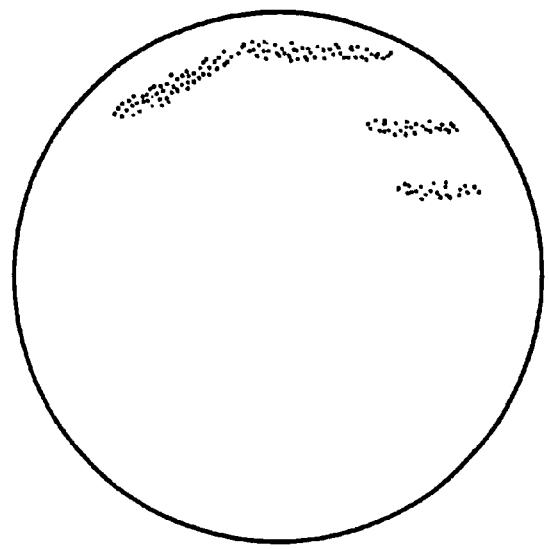

In the input measurement plane, a region corresponding to the sectional area of a fiber flow line having a thickness is filled in. Such a filled-in state is shown in FIG. 25. In FIG. 25, only some of the fiber flow lines have been subjected to the fill-in processing, for the purpose of plain illustration. The radius processing is performed as described heretofore. After the radius processing, the computer returns to the main routine illustrated in FIG. 1 and proceeds to step 10.

In step 10, the computer outputs data obtained after the calculation. That is, results of the analysis are displayed on a computer screen. Results can be printed on a print sheet or the like as needed. Either one of the result of calculation including the radius processing in step 9 and the result of calculation omitting the radius processing can be displayed or printed.

Figure 26:
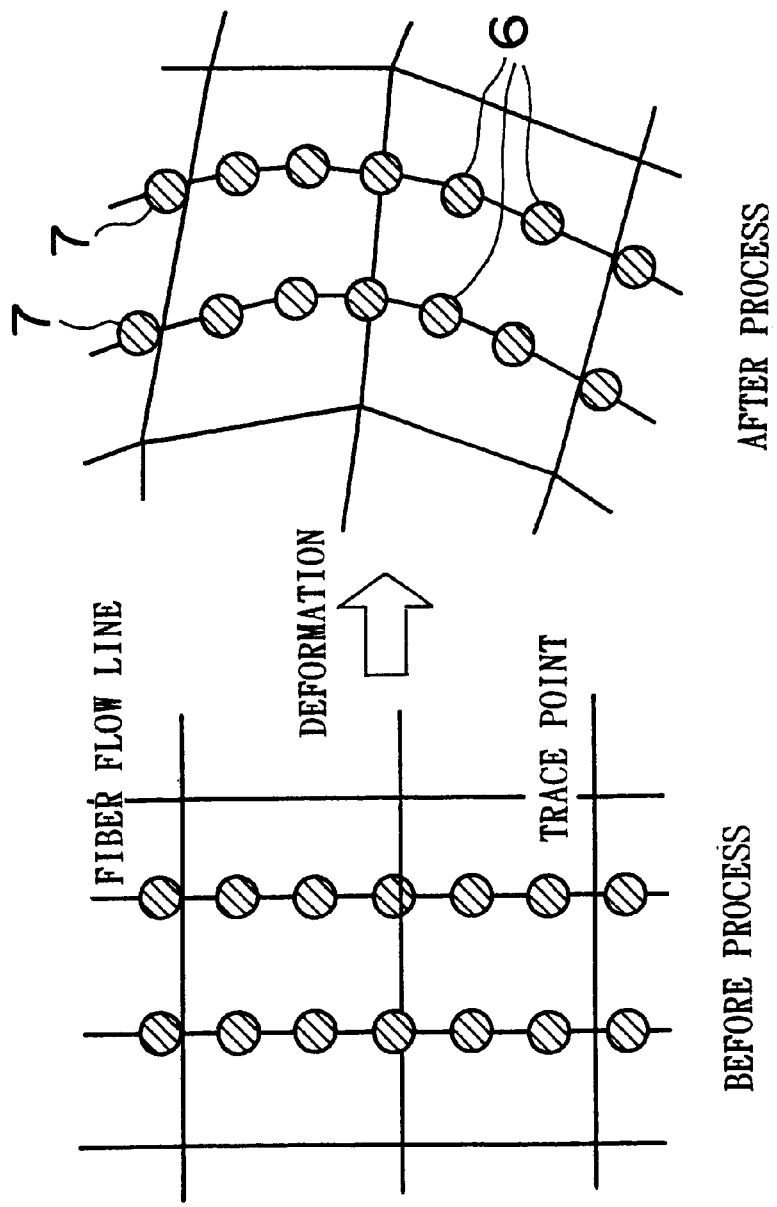
FIG. 26 illustrates trace points and fiber flow lines occurring before and after deformation.

Through the above-described process, a group of trace points occurring before workpiece processing are converted into a group of trace points occurring after workpiece processing, as shown in an example case of FIG. 26. Bent lines 7 passing through the trace points 6 after workpiece processing express fiber flow lines after workpiece processing. The above-described analysis is able to provide good results not only in a case as shown in FIGS. 2 and 3, in which trace points are initially set so as to express fiber flow lines that can actually exist, but also in a case as shown in FIG. 4, in which trace points are initially set so as to express imaginary fiber flow lines that cannot exist in reality.

Figure 27:
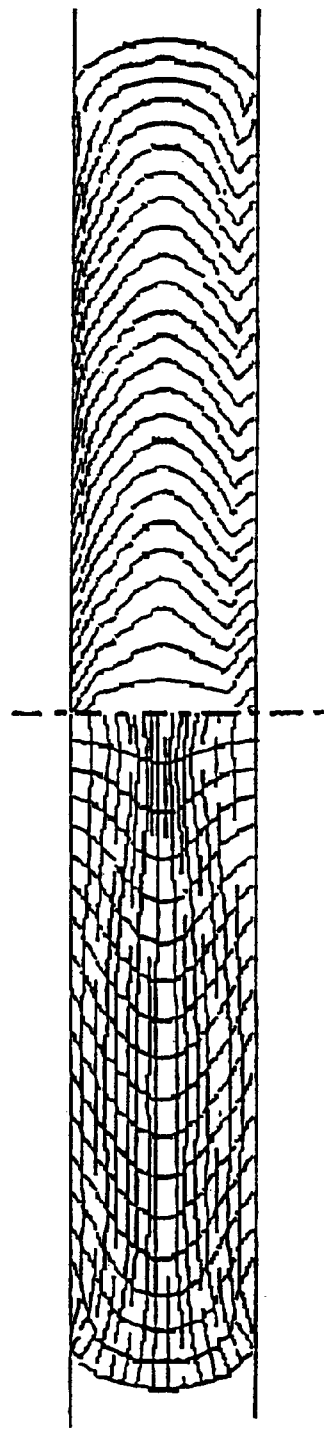
FIG. 27 illustrates results of the analysis of the workpiece having the fiber flow lines shown in FIG. 6.

Results of the analysis performed as described above will be described. FIG. 27 shows, as a first example, results of the analysis of a process in which a workpiece is press-stretched by pressurizing it in a direction of the thickness in a case as shown in FIG. 6, in which fiber flow lines are initially set so as to express distortion that already exits in the workpiece before the process. A right-side half of the view of FIG. 27 indicates that an effect of initial distortion existing before the workpiece process remains after the workpiece process. In particular, the fiber flow lines sharply bend near a lower end face of the workpiece in the right-side half of the view of FIG. 27. This makes it possible to predict an abnormality in material property at the site of sharp bending.

Figure 28:
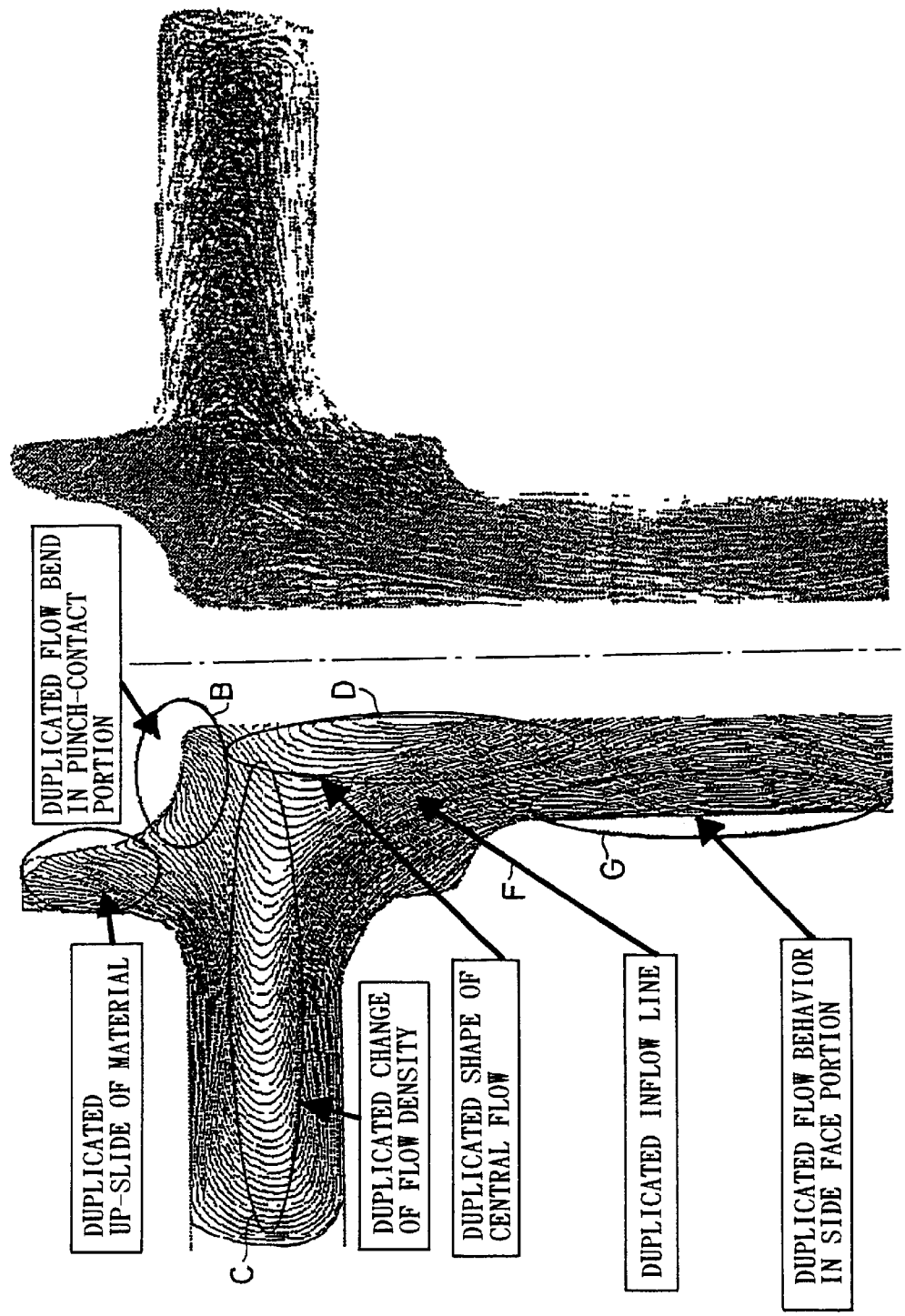
FIG. 28 shows comparison between results of the analysis of an automotive component part and results of observation of a real workpiece.

As a second example, results of the analysis of a process of an automotive component part will be described with reference to FIG. 28. A left-side half of FIG. 28 shows results of the analysis. A right-side half of FIG. 28 shows fiber flow lines in an actual workpiece that has been actually processed. The fiber flow lines were observed after the workpiece was cut, polished and etched. Comparison between the right and left-side halves of FIG. 28 clarifies whether the analysis is good or not. In the example shown in FIG. 28, it can be said that the results of the analysis (left-side half) are excellent. In a region A, the up-slide of the material is duplicated in a good manner. In a region B, the bending of fiber flow lines in a punch-contacting portion is duplicated. In a region C, the changing of the density of fiber flow lines is duplicated. In a region D, the shape of flow of the material in a central portion of the component part is duplicated. Near the distal end of an arrow F, the material inflow lines are duplicated. In a region G, the behavior of fiber flow lines at a side face portion of the component part is duplicated.

Figure 29:
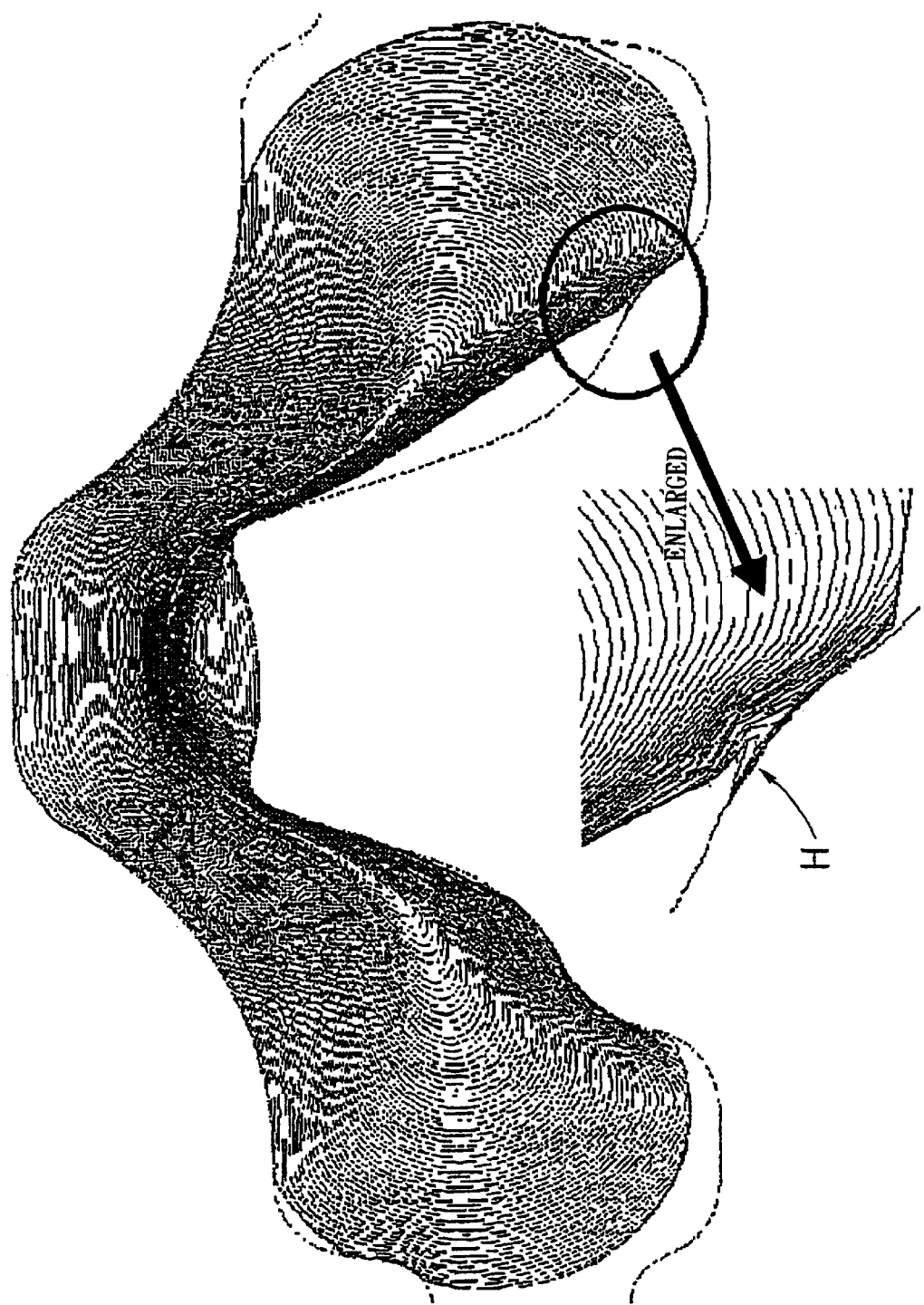
FIG. 29 illustrates results of the analysis of an unusually shaped component part.

As a third example, results of the section analysis (plane distortion) of an unusually shaped component part will be described. FIG. 29 shows results of the analysis. Actual observation of fiber flow lines in a section of the unusually shaped component part is normally difficult. However, the analysis in this embodiment is able to achieve results as shown in FIG. 29. Occurrence of an involute forging defect H can be observed in a circle in a rightward lower portion of FIG. 29. Therefore, it is predicted that actual performance of the process on a real workpiece will create a burr-like defect at the site of the defect H.

Figure 30:
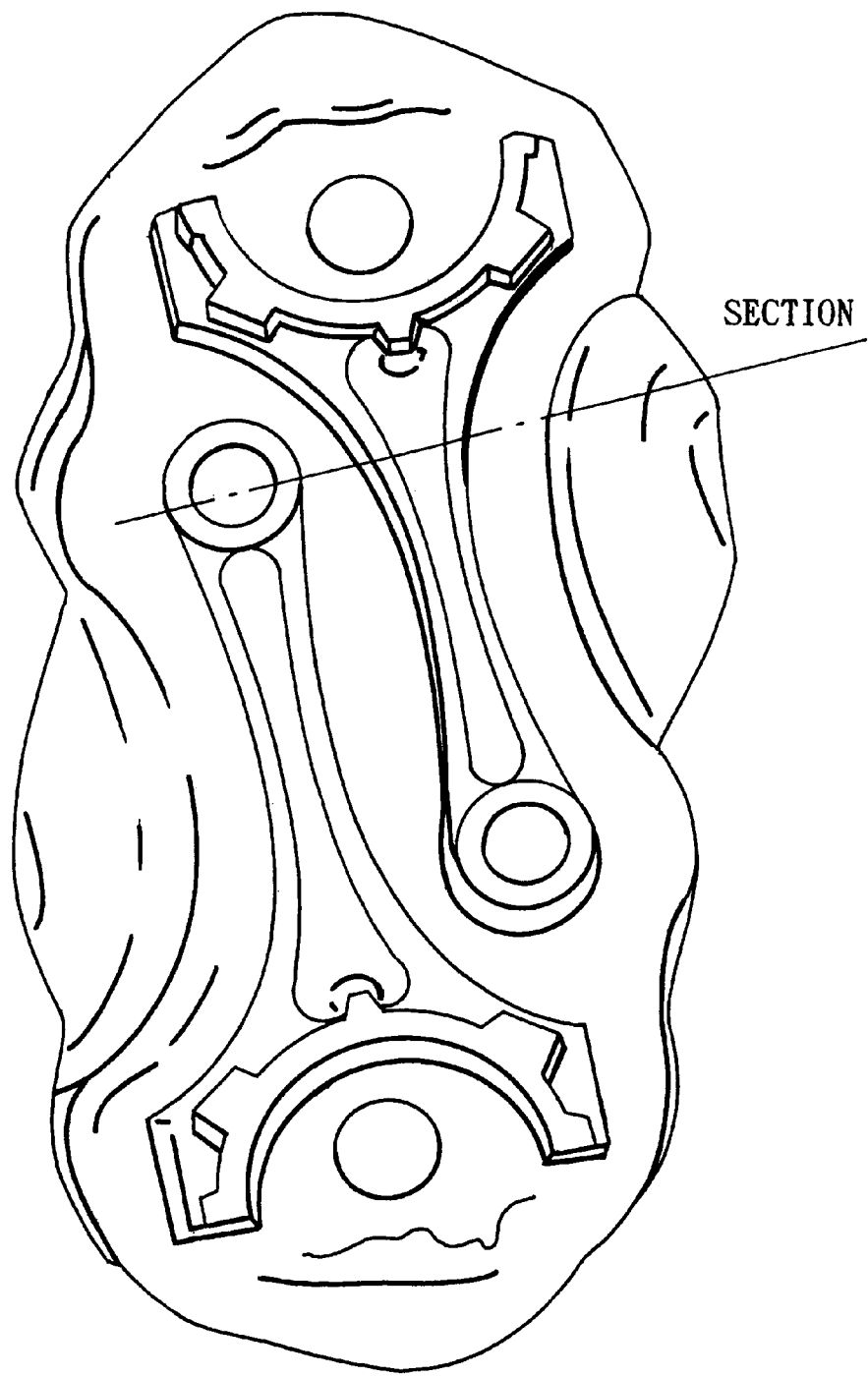
FIG. 30 illustrates a processed state of another automotive component part.
Figure 31:
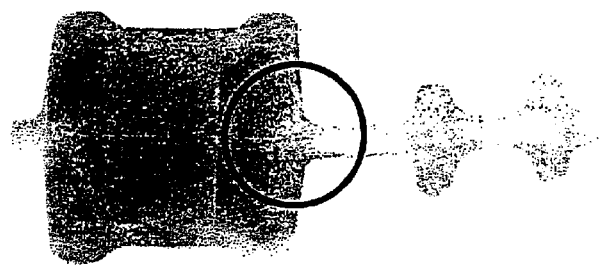
FIG. 31 is a sectional view taken along a broken line in FIG. 30.
Figure 32:
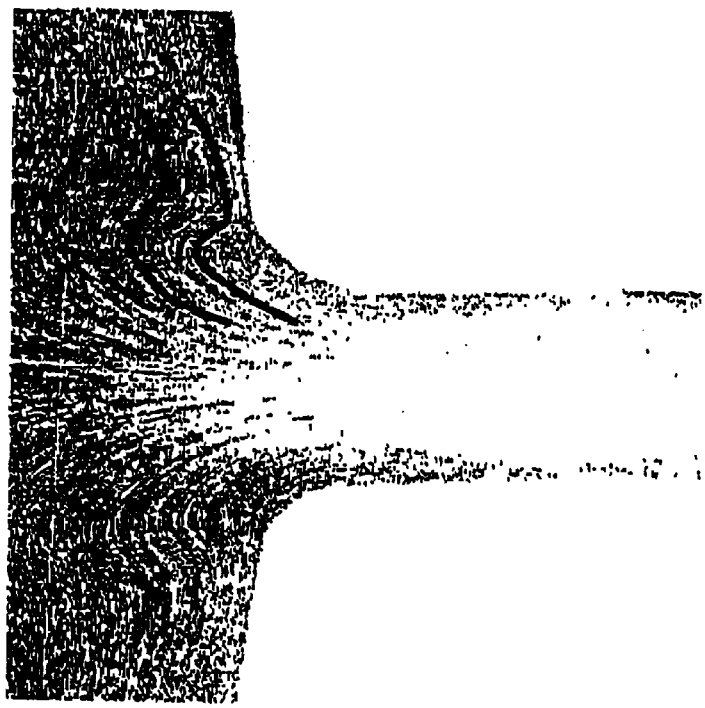
FIG. 32 is an enlarged view of a portion circled in FIG. 31, illustrating results of the analysis of fiber flow lines in that portion.

As a fourth example, results of the analysis of a process of another automotive component part will be described. FIG. 30 shows two component parts formed from a single billet by pressing. FIG. 31 shows a section taken along a broken line in FIG. 30. FIG. 32 shows, in an enlarged view, results of the analysis of the fiber flow lines in a portion circled in FIG. 31. In FIG. 32, irregular fiber flow lines can be seen at a site indicated by thick lines. Therefore, it is predicted that actual performance of the process on a real workpiece will create a forging defect at this site. The analysis results shown in FIGS. 26 through 32 are results achieved without performing the radius processing of the step 9 in the main routine illustrated in FIG. 1.

Figure 33:
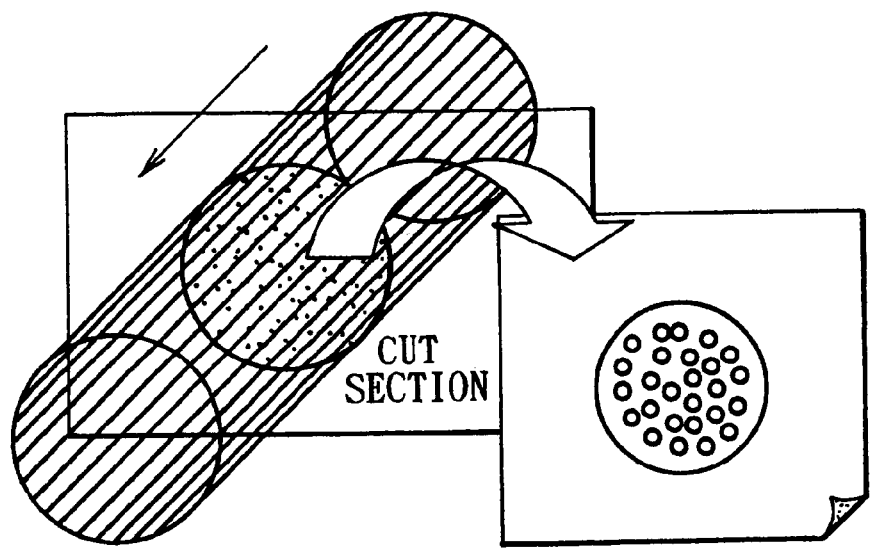
FIG. 33 illustrates the setting of fiber flow lines for a three-dimensional analysis.

As a fifth example, results of a three-dimensional analysis based on the radius processing will be described. When the three-dimensional analysis is to be performed, it is recommended to set, in steps 1 and 2 in the main routine of FIG. 1, fiber flow lines at a substantially uniform density as shown in FIG. 33, simulating the fiber flow that typically occurs in actual workpieces (a billet in this example) before deformation. The plane of a cut section shown in FIG. 33 is perpendicular to the length of the billet and perpendicular to the fiber flow lines. In the sectional view, each fiber flow line has a certain thickness although deformation has not been performed.

After the above-described radius processing is performed in addition to the deformation calculation, results are evaluated. In the measurement plane inputting processing of step 93, a measurement plane can be inputted even if the measurement plane is a plane intersecting a fiber flow line as in the cut section shown in FIG. 33. The filling-in processing of step 94 provides a display such as the display shown in FIG. 25. Although in FIG. 25, the external shape of the section is circular for the purpose of plain illustration, it should be understood that the actual external shape of the section becomes a shape achieved by the deforming process. In FIG. 25, the filled-in fiber flow lines displayed have finite areas. Therefore, the display as shown in FIG. 25 is easier to understand than a display in which fiber flow lines are indicated merely by dots (as in, for example, FIG. 4).

Figure 34:
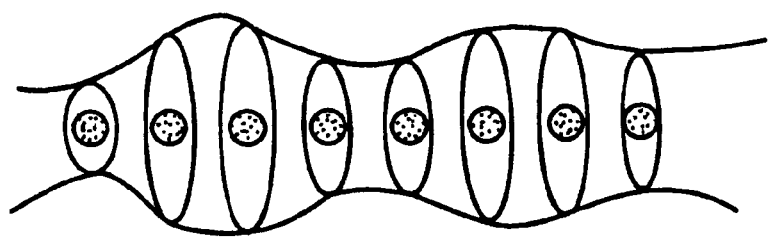
FIG. 34 illustrates a display in which trace points each having an adjusted radius are arranged along a fiber flow line.

When the shape of a filled-in portion is close to a circle, it is considered that the fiber flow line to which the filled-in portion belongs intersects with the measurement plane at an angle close to the right angle. When the shape of a filled-in section of a fiber flow line is an elongated ellipse, the fiber flow line is considered to intersect obliquely with the measurement plane. The sparsity or density of distribution of fiber flow lines after deformation can also be evaluated when results of the radius adjustment described with reference to FIGS. 23 and 24 are also reflected in a display. It is also possible to provide a display as shown in FIG. 34. In the display shown in FIG. 34, trace points on a certain fiber flow line and adjusted radii around the trace points are arranged along the fiber flow line. Utilizing this display, it becomes possible to visually identify a position in the direction of the length of a workpiece at which strong pressurization occurs and a position at which strong pressurization does not occur when a partcular fiber flow line is considered. Furthermore, when the display shown in FIG. 34 is modified so that the fiber flow line bends along the positions after deformation as in the post-process view in FIG. 26, it becomes possible to more specifically understand the condition of deformation.

In this embodiment, the computer sets many trace points in the interior of a workpiece during an initial period of the analysis, as described above. This setting is performed so that the straight or bent lines connecting the trace points express fiber flow lines. Therefore, it is not essential to simulate only fiber flow lines that actually exist in a workpiece. On the contrary, a group of trace points can be set so as to express imaginary fiber flow lines. That is, fiber flow lines can be set even in a plane where it is extremely difficult in reality to observe fiber flow lines, for example, a sectional face perpendicular to the length of a workpiece. Furthermore, it is also possible to set fiber flow lines taking into account the initial distortion caused in a workpiece by processes that have been already performed.

With respect to each set trace point, a displacement involved in deformation caused by a process performed on the workpiece is calculated by applying a technique of a finite element method. By connecting post-deformation trace points, post-deformation fiber flow lines can be expressed. As a result, the forging process of the workpiece can be analyzed More specifically, occurrence of defects, such as a forging defect, dead metal, buckling and the like, can be predicted, and the workability can be evaluated. Furthermore, the residual stress after the process can be predicted in terms of a tendency in distribution of the residual stress although the absolute value thereof cannot be estimated. It also becomes possible to perform the analysis in a plane where it is extremely difficult in reality to observe fiber flow lines, for example, a sectional face perpendicular to the length of a workpiece. Furthermore, it also becomes possible to analyze a post-process effect caused by the initial distortion in a workpiece.

When the distance between adjacent trace points is greater than a predetermined critical value, a new trace point is added between those trace points before the subsequent calculation cycle is continued. Therefore, a high density of trace points can be maintained even in a portion having a high rate of surface area expansion, so that the analysis can be performed with a high precision. As a result, it is unnecessary to indiscriminately increase the trace point density in the initial setting. Hence, the embodiment prevents considerable increases of the calculation time in comparison with the case of a normal finite element method.

Furthermore, the embodiment prevents a trace point from being left behind in a die by performing the interpolating process. Therefore, the embodiment prevents considerable reductions of the analysis precision that would otherwise be caused by the left-behind phenomenon. In order to prevent the left-behind phenomenon, the embodiment converts an element that is likely to experience the left-behind phenomenon, in accordance with the shape of the die, after the positions of the trace points have been updated. Therefore, it is unnecessary to go back one calculation cycle and perform the cycle again in order to prevent the left-behind phenomenon, thereby contributing to minimization of the calculation time. Furthermore, the conversion is applied to all the trace points belonging to that element, so that the crossing of fiber flow lines is also prevented.

After the deformation calculation, each trace point is provided with a radius. By adjusting the radius of each trace point, the embodiment eliminates off-boundary extension and overlap of fiber flow lines. Therefore, each fiber flow line can be displayed not as a mere point but as an area even in a case where the measurement plane is a plane intersecting with post-deformation fiber flow lines. Hence, it becomes possible to select an arbitrary measurement plane regardless of the direction of the post-deformation fiber flow lines. This feature is convenient in three-dimensional evaluation of results of the analysis. The adjusted thickness of fiber flow lines can be used as a basis for evaluation of the sparsity or density of distribution of the post-deformation fiber flow lines. Furthermore, based on the sectional shape of a fiber flow line, the intersecting angle between the fiber flow line and the measurement plane can be evaluated. Further, a display can be achieved in which trace points on a certain fiber flow line and adjusted radii of the trace points are arranged along the fiber flow line. Utilizing this display, it becomes possible to visually identify a position in the direction of the length of a workpiece at which strong pressurization occurs and a position at which strong pressurization does not occur.

Therefore, the embodiment provides a forging process analyzing method which is able to perform high-precision analysis of a forging process while requiring a calculation time that is at most about 5% longer than the calculation time required by a normal finite element method and which is able to facilitate three-dimensional evaluation of results of the analysis, and a medium in which a program for executing the analyzing method is recorded. When the forging process analyzing method is used, results of the analysis can be fed back to the die designing or the production process designing in a turn-around time of only one day or less. Thus, the embodiment contributes to quick process designing.

While the present invention has been described with reference to what is presently considered to be a preferred embodiment thereof, it is to be understood that the embodiment is mere illustrative and that the invention is not limited to the disclosed embodiment or constructions. To the contrary, the invention is intended to cover various modifications and equivalent arrangements without departing from the spirit of the invention. For example, although each of steps 4 (FIG. 8), step 5 (FIG. 10) and step 7 (FIG. 13) in the main routine illustrated in FIG. 1 has a step of determining whether the processing is completed for the entire workpiece, it is possible to combine the determining steps into a single determining step.

What is claimed is:

1. A forging process analyzing method comprising:
   setting a plurality of trace points for expressing at least one fiber flow line in a workpiece that is to be forged by a die;
   calculating an element containing at least one trace point, the element being defined by a plurality of nodes;
   calculating a displacement of each of the nodes of the element due to deformation of the workpiece;
   calculating a displacement of each trace point contained in the element based on the displacements of the nodes of the element; and
   expressing at least one post-deformation fiber flow line in the workpiece by connecting the trace points after displacement.

2. A forging process analyzing method according to claim 1, further comprising setting a new trace point between trace points in a portion that has a high rate of expansion caused by deformation.

3. A forging process analyzing method according to claim 2, further comprising:
   comparing a distance between adjacent trace points present on a fiber flow line with a predetermined value; and
   setting a new trace point when the distance between the adjacent trace points exceeds the value.

4. A forging process analyzing method according to claim 1, further comprising:
   converting, when there is a trace point that is to be left behind in a die due to deformation, an element containing the trace point into a correction element in which an element side extending in a shape of the die is replaced by a line expressing the shape of the die; and
   correcting, through conversion of the element, positions of all trace points present in the element that contains the trace point to be left behind.

5. A forging process analyzing method according to claim 4,
   wherein when the line expressing the shape of the die extends in an outermost peripheral element of the workpiece, the outermost peripheral element is converted, and
   wherein the positions of all the trace points present in the element are corrected.

6. A forging process analyzing method according to claim 1, wherein a fiber flow line expressed by connecting trace points is present in a sectional face of the workpiece perpendicular to a length of the workpiece.

7. A forging process analyzing method according to claim 1, wherein the trace points are set by imitating a real fiber flow line, and a fiber flow line having a thickness is expressed by providing each trace point after displacement with a radius.

8. A forging process analyzing method according to claim 7, wherein the radius of a trace point is adjusted.

9. A forging process analyzing method according to claim 8, wherein a portion of a fiber flow line extending off a boundary of the workpiece is eliminated by radius adjustment, so that the fiber flow line is contained within the boundary of the workpiece.

10. A forging process analyzing method according to claim 7, wherein overlap between fiber flow lines is eliminated by radius adjustment.

11. A forging process analyzing method according to claim 7, wherein a section of the workpiece after deformation is displayed, and wherein in a display of the section, an interior of the fiber flow line having a thickness is filled in.

12. A forging process analyzing method according to claim 1, wherein said calculating a displacement of each of the nodes is performed according to a Lagrangian finite element method.

13. A mechanically readable medium storing a program for causing a computer to execute:
   a procedure of setting a plurality of trace points for expressing at least one fiber flow line in a workpiece that is to be forged by a die;
   a procedure of calculating an element containing at least one trace point, the element being defined by a plurality of nodes;
   a procedure of calculating a displacement of each of the nodes of the element due to deformation of the workpiece;
   a procedure of calculating a displacement of each trace point contained in the element based on the displacements of the nodes of the element; and
   a procedure of expressing at least one post-deformation fiber flow line in the workpiece by connecting the trace points after displacement.

14. A mechanically readable medium according to claim 13, wherein the program also causes the computer to execute a procedure of setting a new trace point between trace points in a portion that has a high rate of expansion caused by deformation.

15. A mechanically readable medium according to claim 14, wherein the program compares a distance between adjacent trace points present on a fiber flow line with a predetermined value, and the program sets a new trace point when the distance between the adjacent trace points exceeds the value.

16. A mechanically readable medium according to claim 13,
   wherein, when there is a trace point that is to be left behind in a die due to deformation, the program converts an element containing the trace point into a correction element in which an element side extending in a shape of the die is replaced by a line expressing the shape of the die, and
   wherein the program corrects, through conversion of the element, positions of all trace points present in the element that contains the trace point to be left behind.

17. A mechanically readable medium according to claim 13, wherein when the line expressing the shape of the die extends in an outermost peripheral element of the workpiece, the program converts the outermost peripheral element, and corrects the positions of all the trace points present in the element.

18. A mechanically readable medium according to claim 12, wherein a fiber flow line expressed by connecting trace points is present in a sectional face of the workpiece perpendicular to a length of the workpiece.

19. A mechanically readable medium according to claim 13, wherein the program sets the trace points by imitating a real fiber flow line, and the program expresses a fiber flow line having a thickness by providing each trace point after displacement with a radius.

20. A mechanically readable medium according to claim 19, wherein the program adjusts the radius of a trace point.

21. A mechanically readable medium according to claim 20, wherein the program eliminates a portion of a fiber flow line extending off a boundary of the workpiece through radius adjustment, so that the fiber flow line is contained within the boundary of the workpiece.

22. A mechanically readable medium according to claim 19, wherein the program eliminates overlap between fiber flow lines through radius adjustment.

23. A mechanically readable medium according to claim 19, wherein the program displays a section of the workpiece after deformation and, in a display of the section, fills in an interior of the fiber flow line having a thickness.

24. A mechanically readable medium according to claim 13, wherein said procedure of calculating a displacement of each of the nodes is performed according to a Lagrangian finite element method.

* * * * *